(12) United States Patent
Mullah et al.

(10) Patent No.: US 7,414,118 B1
(45) Date of Patent: Aug. 19, 2008

(54) MODIFIED OLIGONUCLEOTIDES AND APPLICATIONS THEREOF

(75) Inventors: Khairuzzaman Bashar Mullah, Union City, CA (US); Zhaochun Ma, San Carlos, CA (US)

(73) Assignee: Applied Biosystems Inc., Foster City, CA (US)

( * ) Notice: Subject to any disclaimer, the term of this patent is extended or adjusted under 35 U.S.C. 154(b) by 83 days.

(21) Appl. No.: 11/372,984

(22) Filed: Mar. 9, 2006

Related U.S. Application Data

(63) Continuation of application No. 11/106,045, filed on Apr. 14, 2005, now abandoned.

(60) Provisional application No. 60/562,621, filed on Apr. 14, 2004.

(51) Int. Cl.
*C07H 21/02* (2006.01)
*C07H 21/04* (2006.01)
*C12Q 1/68* (2006.01)
*C07H 19/04* (2006.01)

(52) U.S. Cl. .................. 536/23.1; 536/24.3; 536/24.33; 536/26.6; 435/6

(58) Field of Classification Search ................ 536/23.1, 536/24.3, 24.44, 26.6; 435/6
See application file for complete search history.

(56) References Cited

OTHER PUBLICATIONS

Englisch et al. Angew. Chem. Int. Ed. Engl. vol. 30, No. 6, Jun. 1991, pp. 613-722.*

\* cited by examiner

*Primary Examiner*—Jezia Riley
(74) *Attorney, Agent, or Firm*—Vincent M. Powers; Shirley A. Recipon

(57) ABSTRACT

Disclosed, among other things, are primers containing certain modified nucleobases in the 3′ terminal region of the primers that provide reduced formation of primer-dimers during amplification reactions, and various methods of use thereof.

19 Claims, No Drawings

```
                        SEQUENCE LISTING

<160> NUMBER OF SEQ ID NOS: 29

<210> SEQ ID NO 1
<211> LENGTH: 26
<212> TYPE: DNA
<213> ORGANISM: Artificial
<220> FEATURE:
<223> OTHER INFORMATION: Synthetic DNA

<400> SEQUENCE: 1
ggtcagttaa taaccacctt tcaccc                                          26

<210> SEQ ID NO 2
<211> LENGTH: 19
<212> TYPE: DNA
<213> ORGANISM: Artificial
<220> FEATURE:
<223> OTHER INFORMATION: Synthetic DNA

<400> SEQUENCE: 2
gccaggaggc agaggatgg                                                  19

<210> SEQ ID NO 3
<211> LENGTH: 20
<212> TYPE: DNA
<213> ORGANISM: Artificial
<220> FEATURE:
<223> OTHER INFORMATION: Synthetic DNA

<400> SEQUENCE: 3
ggagaccccg aaagaaagcc                                                 20

<210> SEQ ID NO 4
<211> LENGTH: 16
<212> TYPE: DNA
<213> ORGANISM: Artificial
<220> FEATURE:
<223> OTHER INFORMATION: Synthetic DNA

<400> SEQUENCE: 4
aggcgtggtg ggctgg                                                     16

<210> SEQ ID NO 5
<211> LENGTH: 26
<212> TYPE: DNA
<213> ORGANISM: Artificial
<220> FEATURE:
<223> OTHER INFORMATION: Synthetic DNA

<400> SEQUENCE: 5
catatctcac tcctaaaacc cacagg                                          26

<210> SEQ ID NO 6
<211> LENGTH: 20
<212> TYPE: DNA
```

```
<213> ORGANISM: Artificial
<220> FEATURE:
<223> OTHER INFORMATION: Synthetic DNA

<400> SEQUENCE: 6
cagacaccta ccacctgccc                                              20

<210> SEQ ID NO 7
<211> LENGTH: 20
<212> TYPE: DNA
<213> ORGANISM: Artificial
<220> FEATURE:
<223> OTHER INFORMATION: Synthetic DNA

<400> SEQUENCE: 7
ggagaccccg aaagaaagcc                                              20

<210> SEQ ID NO 8
<211> LENGTH: 16
<212> TYPE: DNA
<213> ORGANISM: Artificial
<220> FEATURE:
<223> OTHER INFORMATION: Synthetic DNA

<400> SEQUENCE: 8
aggcgtggtg ggctgg                                                  16

<210> SEQ ID NO 9
<211> LENGTH: 26
<212> TYPE: DNA
<213> ORGANISM: Artificial
<220> FEATURE:
<223> OTHER INFORMATION: Synthetic DNA

<400> SEQUENCE: 9
ggtcagttaa taaccacctt tcaccc                                       26

<210> SEQ ID NO 10
<211> LENGTH: 19
<212> TYPE: DNA
<213> ORGANISM: Artificial
<220> FEATURE:
<223> OTHER INFORMATION: Synthetic DNA

<400> SEQUENCE: 10
gccaggaggc agaggatgg                                               19

<210> SEQ ID NO 11
<211> LENGTH: 20
<212> TYPE: DNA
<213> ORGANISM: Artificial
<220> FEATURE:
<223> OTHER INFORMATION: Synthetic DNA

<400> SEQUENCE: 11
ggagaccccg aaagaaagcc                                              20

<210> SEQ ID NO 12
<211> LENGTH: 16
<212> TYPE: DNA
<213> ORGANISM: Artificial
<220> FEATURE:
<223> OTHER INFORMATION: Synthetic DNA

<400> SEQUENCE: 12
aggcgtggtg ggctgg                                                  16
```

```
<210> SEQ ID NO 13
<211> LENGTH: 24
<212> TYPE: DNA
<213> ORGANISM: Artificial
<220> FEATURE:
<223> OTHER INFORMATION: Synthetic DNA

<400> SEQUENCE: 13
atcagaaacg aacgcatcat caag                                          24

<210> SEQ ID NO 14
<211> LENGTH: 24
<212> TYPE: DNA
<213> ORGANISM: Artificial
<220> FEATURE:
<223> OTHER INFORMATION: Synthetic DNA

<400> SEQUENCE: 14
aaacagccac aaagccagcc ggaa                                          24

<210> SEQ ID NO 15
<211> LENGTH: 25
<212> TYPE: DNA
<213> ORGANISM: Artificial
<220> FEATURE:
<223> OTHER INFORMATION: Synthetic DNA

<400> SEQUENCE: 15
gctctctgga cttcacagaa ctgga                                         25

<210> SEQ ID NO 16
<211> LENGTH: 24
<212> TYPE: DNA
<213> ORGANISM: Artificial
<220> FEATURE:
<223> OTHER INFORMATION: Synthetic DNA

<400> SEQUENCE: 16
ccttaccttg gaagtggacg tagg                                          24

<210> SEQ ID NO 17
<211> LENGTH: 25
<212> TYPE: DNA
<213> ORGANISM: Artificial
<220> FEATURE:
<223> OTHER INFORMATION: Synthetic DNA

<400> SEQUENCE: 17
gctctctgga cttcacagaa ctgga                                         25

<210> SEQ ID NO 18
<211> LENGTH: 24
<212> TYPE: DNA
<213> ORGANISM: Artificial
<220> FEATURE:
<223> OTHER INFORMATION: Synthetic DNA

<400> SEQUENCE: 18
ccttaccttg gaagtggacg tagg                                          24

<210> SEQ ID NO 19
<211> LENGTH: 25
<212> TYPE: DNA
<213> ORGANISM: Artificial
<220> FEATURE:
```

-continued

```
<223> OTHER INFORMATION: Synthetic DNA

<400> SEQUENCE: 19
gctctctgga cttcacagaa ctgga                                    25

<210> SEQ ID NO 20
<211> LENGTH: 24
<212> TYPE: DNA
<213> ORGANISM: Artificial
<220> FEATURE:
<223> OTHER INFORMATION: Synthetic DNA

<400> SEQUENCE: 20
ccttaccttg gaagtggacg tagg                                     24

<210> SEQ ID NO 21
<211> LENGTH: 20
<212> TYPE: DNA
<213> ORGANISM: Artificial
<220> FEATURE:
<223> OTHER INFORMATION: Synthetic DNA

<400> SEQUENCE: 21
ggtcagttaa taaccacctt                                          20

<210> SEQ ID NO 22
<211> LENGTH: 19
<212> TYPE: DNA
<213> ORGANISM: Artificial
<220> FEATURE:
<223> OTHER INFORMATION: Synthetic DNA

<400> SEQUENCE: 22
ggtcagttaa taaccacct                                           19

<210> SEQ ID NO 23
<211> LENGTH: 20
<212> TYPE: DNA
<213> ORGANISM: Artificial
<220> FEATURE:
<223> OTHER INFORMATION: Synthetic DNA

<400> SEQUENCE: 23
ggtcagttaa taaccacctt                                          20

<210> SEQ ID NO 24
<211> LENGTH: 19
<212> TYPE: DNA
<213> ORGANISM: Artificial
<220> FEATURE:
<223> OTHER INFORMATION: Synthetic DNA

<400> SEQUENCE: 24
gccaggaggc agaggatgg                                           19

<210> SEQ ID NO 25
<211> LENGTH: 19
<212> TYPE: DNA
<213> ORGANISM: Artificial
<220> FEATURE:
<223> OTHER INFORMATION: Synthetic DNA

<400> SEQUENCE: 25
gccaggaggc agaggaggt                                           19
```

```
<210> SEQ ID NO 26
<211> LENGTH: 20
<212> TYPE: DNA
<213> ORGANISM: Artificial
<220> FEATURE:
<223> OTHER INFORMATION: Synthetic DNA

<400> SEQUENCE: 26
ctcaccctca tggcctcatt                                              20

<210> SEQ ID NO 27
<211> LENGTH: 20
<212> TYPE: DNA
<213> ORGANISM: Artificial
<220> FEATURE:
<223> OTHER INFORMATION: Synthetic DNA

<400> SEQUENCE: 27
ctcaccctca tggcctcatt                                              20

<210> SEQ ID NO 28
<211> LENGTH: 20
<212> TYPE: DNA
<213> ORGANISM: Artificial
<220> FEATURE:
<223> OTHER INFORMATION: Synthetic DNA

<400> SEQUENCE: 28
ctcaccctca tggcctcatt                                              20

<210> SEQ ID NO 29
<211> LENGTH: 19
<212> TYPE: DNA
<213> ORGANISM: Artificial
<220> FEATURE:
<223> OTHER INFORMATION: Synthetic DNA

<400> SEQUENCE: 29 acctcccaa cggccaaat                                                19
```

MODIFIED OLIGONUCLEOTIDES AND APPLICATIONS THEREOF

This application is a continuation of U.S. patent application Ser. No. 11/106,045, filed Apr. 14, 2005, and claims a priority benefit under 35 U.S.C. §119(e) from U.S. Patent Application No. 60/562,621, filed Apr. 14, 2004, which are incorporated herein by reference.

The present teachings relate to nucleic acid amplification, for example, compounds and methods for application in the polymerase chain reaction (PCR).

Detecting the presence of target nucleic acids plays an important role in a variety for applications in diverse fields, including: medical diagnostics, forensic science and genetic analysis. PCR is an example of a nucleic acid amplification method that can provide a highly sensitive means for detecting the presence of target nucleic acids by selective amplification of a target nucleic acid sequence.

A significant problem with nucleic acid amplifications such as PCR is the generation of non-specific amplification products. One example of a non-specific amplification process that can be problematic in PCR reactions is "primer-dimer" amplification. Primer-dimer amplification can result when, for example, the 3' terminal region of a primer has some degree of complimentarily with itself or another primer. Such primers will hybridize to one another to form primer-dimers. Amplification of the primer-dimer will then lead to primer-dimer amplicons that can in turn act as templates for further amplification. One outcome of such a process being a depletion of primers resulting in reduced sensitivity or even a failure to amplify the intended target nucleic acid.

To complicate the problem, it is well known that the addition of a large excess of primers during PCR reactions allows even weak complimentarily at the 3' terminal region to result in primer-dimer amplicons. As a result there is a need to develop reagents and methods that suppress primer-dimer formation in amplification reactions such as PCR.

It has now been found that, surprisingly, incorporation of certain modified nucleobases in the 3' terminal region of primers can have beneficial impact on the formation of primer-dimer amplicons during amplification reactions.

In some embodiments the present teachings provide for polynucleotides comprising at least one modified pyrimidine nucleobase comprising the structure

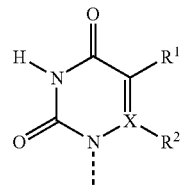

where X can be N or C, $R^1$ can be selected from —H, —F, —Cl, —Br, $C_1$-$C_6$ alkyl, $C_1$-$C_6$ substituted alkyl, $C_3$-$C_{10}$ aryl, $C_3$-$C_{10}$ substituted aryl, —$CF_3$, —$CF_2H$, —$CF_2CH_3$, —$CF_2CF_3$, $CCl_3$, —CN, —CHO, —$CO_2R$, —$SO_3R$, —$PO_3RR$, —C(O)NRR, azido, and —$NO_2$, and $R^2$ can be selected from —H, —F, —Cl, —Br, $C_1$-$C_6$ alkyl, $C_1$-$C_6$ substituted alkyl, $C_3$-$C_{10}$ aryl, $C_3$-$C_{10}$ substituted aryl, —$CF_3$, —$CF_2H$, —$CF_2CH_3$, —$CF_2CF_3$, —$CCl_3$, —CN, —CHO, —$CO_2R$, —$SO_3R$, —$PO_3RR$, —C(O)NRR, azido, and —$NO_2$, where each R is independently —H, $C_1$-$C_6$ alkyl or $C_3$-$C_{10}$ aryl or alkylaryl, such that at least one of $R^1$ or $R^2$ is an electron withdrawing substituent or X is N, such that when X is N, $R^2$ is absent, and at least one said modified pyrimidine nucleobase is no more than 4 nucleotides from the 3' terminus of the polynucleotide. In some embodiments, X can be C. In some embodiments, X is C and $R^2$ is —H. In some embodiments, X is C, $R^2$ is —H and $R^1$ can be selected from —F, —Cl, —Br, —$CO_2R$, —$NO_2$, —CHO, —$COCH_3$, —$CF_3$, —$CF_2H$, azido, or —CN wherein R is defined as above. In some embodiments, X is C, $R^2$ is —H and $R^1$ is —F. In some embodiments, X is C, $R^2$ is —H and $R^1$ is —$CF_3$. In some embodiments, X is C, $R^2$ is —H and $R^1$ is —CN. In some embodiments, X is C, $R^2$ is —H and $R^1$ is —Cl. In some embodiments, X is C, $R^2$ is —H and $R^1$ is —$CO_2R$, wherein R is defined as above. In some embodiments, X is C, $R^2$ is —H and $R^1$ is —$NO_2$. In some embodiments, X is C, $R^2$ is —H and $R^1$ is —CHO. In some embodiments, X is C, $R^2$ is —H and $R^1$ is —$COCH_3$. In some embodiments, X is C, $R^2$ is —H and $R^1$ is —$CF_2H$. In some embodiments, X is C, $R^2$ is —H and $R^1$ is —Br.

In some embodiments, $R^1$ is —H. In some embodiments, $R^1$ is —H and X is C. In some embodiments, $R^1$ is —H, X is C and $R^2$ can be selected from —F, —Cl, —Br, —$CO_2R$, —$NO_2$, —CHO, —$SO_3R$, —$PO_3RR$—$C(O)CH_3$, —$CF_3$, —$CF_2H$, azido, and —CN, wherein R is defined as above. In some embodiments, $R^1$ is —H, X is C and $R^2$ is —F. In some embodiments, $R^1$ is —H, X is C and $R^2$ is —Cl. In some embodiments, $R^1$ is —H, X is C and $R^2$ is —Br. In some embodiments, $R^1$ is —H, X is C and $R^2$ is —$CO_2R$, wherein R is defined as above. In some embodiments, $R^1$ is —H, X is C and $R^2$ is —$NO_2$. In some embodiments, $R^1$ is —H, X is C and $R^2$ is —CHO. In some embodiments, $R^1$ is —H, X is C and $R^2$ is —$SO_3R$, wherein R is defined as above. In some embodiments, $R^1$ is —H, X is C and $R^2$ is —$PO_3RR$, wherein R is defined as above. In some embodiments, $R^1$ is —H, X is C and $R^2$ is —$C(O)CH_3$. In some embodiments, $R^1$ is —H, X is C and $R^2$ is —$CF_3$. In some embodiments, $R^1$ is —H, X is C and $R^2$ is —$CF_2H$. In some embodiments, $R^1$ is —H, X is C and $R^2$ is —CN.

In some embodiments, X can be N. In some embodiments, X is N and $R^1$ is selected from —F, —Cl, —Br, —CHO, azido, and —$CF_3$. In some embodiments, X is N and $R^1$ is —F. In some embodiments, X is N and $R^1$ is —Cl. In some embodiments, X is N and $R^1$ is —Br. In some embodiments, X is N and $R^1$ is —CHO. In some embodiments, X is N and $R^1$ is —$CF_3$.

In some embodiments, the modified pyrimidine nucleobase can be selected from

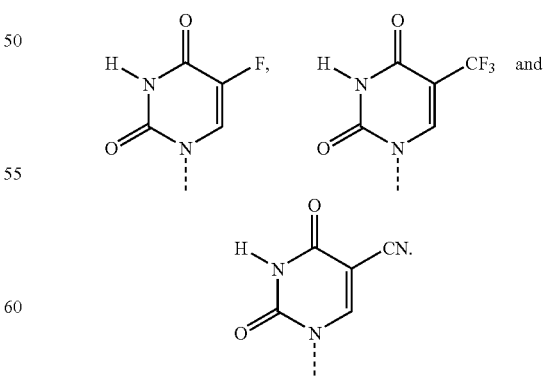

In some embodiments, the at least one modified pyrimidine nucleobase is no more than 3 nucleotides from the 3' terminus of the polynucleotide. In some embodiments, the at least one modified pyrimidine nucleobase is no more than 2 nucleotides from the 3' terminus of the polynucleotide. In some embodiments, the at least one modified nucleotide is the 3' terminal nucleotide of the polynucleotide.

In some embodiments, polynucleotides of the present teachings can be primers in, for example, primer extension reactions. In some embodiments, polynucleotides of the present teachings are extendable at the 3'-terminus.

In some embodiments, polynucleotides of the present teachings can comprise at least one of a detectable label, a quencher or a minor groove binder. In some embodiments, polynucleotides of the present teachings can serve as probes.

In some embodiments, the present teachings provide for methods of primer extension comprising, annealing a polynucleotide primer to a denatured DNA template such that, the polynucleotide primer anneals to a complementary polynucleotide sequence on a strand of the denatured DNA template to form a primer-template complex, and extending the primer portion of the primer-template complex to form a double stranded amplicon, wherein the polynucleotide primer is a primer according to the present teachings.

In some embodiments, the present teachings provide for methods of primer extension comprising, after the step of extending, denaturing the double stranded amplicon. In some embodiments, the steps of annealing, extending and denaturing can be repeated at least one time. In some embodiments, the steps of annealing, extending and denaturing can be repeated at least 10 times. In some embodiments, the steps of annealing, extending and denaturing can be repeated at least 20 times. In some, embodiments, the steps of annealing, extending and denaturing can be repeated at least 30 times. In some embodiments, the steps of annealing, extending and denaturing can be repeated at least 40 times.

In some embodiments, the present teachings provide for methods of primer extension, wherein the extending takes place in the presence of extendable nucleotide triphosphates and non-extendable nucleotide triphosphates to form DNA amplicon fragments. In some embodiments the method of primer extension comprises, detecting the DNA amplicon fragments.

In some embodiments, the present teachings provide methods of primer extension comprising: i) annealing a first polynucleotide primer and a second polynucleotide primer to a first and second strand of a denatured DNA template such that, the first polynucleotide primer anneals to a complementary oligonucleotide sequence on the first strand of the denatured DNA template and the second polynucleotide primer anneals to a complementary oligonucleotide sequence on the second strand of the denatured DNA template to form a first and a second primer-template complex, and ii) extending the primer portion of at least one of the first and second primer-template complex to form double stranded DNA amplicon, where at least one of the first polynucleotide primer or the second polynucleotide primer can be a polynucleotide according to the present teachings.

In some embodiments, the present teachings provide methods of primer extension comprising, prior to the step of annealing, forming a mixture comprising a first polynucleotide primer, a second polynucleotide primer, a DNA template, and other primer extension reagents. In some embodiments, the present teachings provide methods of primer extension comprising, after the step of forming but prior to the step of annealing, denaturing the DNA template to form a first strand of denatured DNA template and a second denatured DNA template. In some embodiments, the present teachings provide methods of primer extension comprising, after the step of extending, denaturing the double stranded DNA amplicon.

In some embodiments, the steps of annealing, extending and denaturing the double stranded DNA amplicon can optionally be repeated from 1-100 times. Optionally, the steps of annealing, extending and denaturing the double stranded DNA amplicon can be repeated from 1-50 times. It will be understood that the present teachings encompass all possible ranges for repeating the steps of annealing, extending and denaturing the double stranded DNA amplicon between 1 and 100 times. That is, the steps of annealing, extending and denaturing the double stranded DNA amplicon can be repeated from 1 time up to 100 times and any number of times in between. For example, the range, of 1-10 will be understood to include all possible ranges using all integers between 1 and 10, i.e.—1, 2, 3, 4, 5, 6, 7, 8, 9, 10. In some embodiments, the steps of annealing, extending and denaturing the double stranded DNA amplicon can optionally be repeated greater than 1 time. In some embodiments, the steps of annealing, extending and denaturing the double stranded DNA amplicon can optionally be repeated greater than 10 times. In some embodiments, the steps of annealing, extending and denaturing the double stranded DNA amplicon can optionally be repeated greater than 20 times. In some embodiments, the steps of annealing, extending and denaturing the double stranded DNA amplicon can optionally be repeated greater than 30 times. In some embodiments, the steps of annealing, extending and denaturing the double stranded DNA amplicon can optionally be repeated greater than 40 times. In some embodiments, the steps of annealing, extending and denaturing the double stranded DNA amplicon can optionally be repeated greater than 50 times.

In some embodiments, the present teachings provide for methods of primer extension comprising, prior to the step of extending the primer portion, annealing a polynucleotide probe to a first or second strand of a denatured DNA template such that, the polynucleotide probe anneals to a complementary polynucleotide sequence on the first strand of the denatured DNA template and/or the polynucleotide probe anneals to a complementary oligonucleotide sequence on the second strand of the denatured DNA template. In some embodiments, the polynucleotide probe comprises at least one detectable label. In some embodiments, the polynucleotide probe further comprises at least one of a quencher, a minor groove binder or both. In some embodiments, the polynucleotide probe can be a polynucleotide of the present teachings.

In some embodiments, the present teachings provide methods of oligonucleotide ligation comprising, i) forming a complex comprising a first and a second polynucleotide strand annealed to a DNA template such that, the first polynucleotide strand anneals to a first complementary polynucleotide sequence on the strand of the denatured DNA template and the second polynucleotide strand anneals to a second complementary polynucleotide sequence on the strand of the denatured DNA template, wherein the second complementary polynucleotide sequence on the strand of the denatured DNA template is located 5' to the first complementary polynucleotide sequence on the strand of the denatured DNA template, and ii) forming a stable covalent bond between the first and second polynucleotide strands, wherein at least one of the first polynucleotide strand or the second polynucleotide strand is a polynucleotide of the present teachings.

In some embodiments, the present teachings provide for methods for detecting a target polynucleotide sequence comprising, (a) reacting a target polynucleotide strand with a first probe pair comprising (i) a first polynucleotide probe containing a sequence that is complementary to a first target region in the target strand and (ii) a second polynucleotide probe comprising a sequence that is complementary to a second target region in the target strand, wherein the second region is located 5' to the first region and overlaps the first region by at least one nucleotide base, under conditions effective for the first and second probes to hybridize to the first and second regions in the target strand, respectively, forming a first hybridization complex, (b) cleaving the second probe in the first hybridization complex, to form a second hybridization complex comprising the target strand, the first probe, and a first fragment of the second probe having a 5' terminal nucleotide located immediately contiguous to a 3' terminal nucleotide of the first probe, (c) ligating the first probe to the hybridized fragment of the second probe to form a first ligated strand hybridized to the target strand, (d) denaturing the first ligated strand from the target strand, and (e) performing one or more additional cycles of steps (a) through (d), with the proviso that in the last cycle, step (d) is optionally omitted, wherein at least one of the first probe, the second probe or both is a polynucleotide comprising at least one modified pyrimidine nucleobase comprising the structure

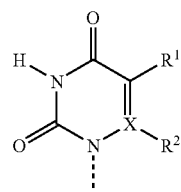

where X can be N or C, $R^1$ can be selected from —H, —F, —Cl, —Br, $C_1$-$C_6$ alkyl, $C_1$-$C_6$ substituted alkyl, $C_3$-$C_{10}$ aryl, $C_3$-$C_{10}$ substituted aryl, —$CF_3$, —$CF_2H$, —$CF_2CH_3$, —$CF_2CF_3$, —$CCl_3$, —CN, —CHO, —$CO_2R$, —$SO_3R$, —$PO_3RR$, —C(O)NPR, azido, and —$NO_2$, and $R^2$ can be selected from —H, —F, —Cl, —Br, $C_1$-$C_6$ alkyl, $C_1$-$C_6$ substituted alkyl, $C_3$-$C_{10}$ aryl, $C_3$-$C_{10}$ substituted aryl, —$CF_3$, —$CF_2H$, —$CF_2CH_3$, —$CF_2CF_3$, —$CCl_3$, —CN, —CHO, —$CO_2R$, —$SO_3R$, —$PO_3RR$, —C(O)NRR, azido, and —$NO_2$ where each R is independently —H, $C_1$-$C_6$ alkyl or $C_3$-$C_{10}$ aryl or alkylaryl, such that at least one of $R^1$ or $R^2$ is an electron withdrawing substituent or X is N, such that when X is N, $R^2$ is absent, and at least one said modified pyrimidine nucleobase is no more than 4 nucleotides from the 3' terminus of the polynucleotide. In some embodiments, the modified pyrimidine nucleobase can be selected from

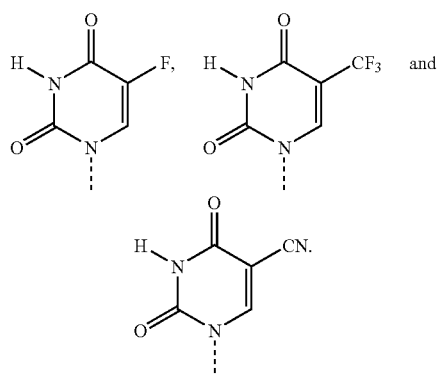

In some embodiments, at least one said modified purine nucleobase is no more than 2 nucleotides from the 3' terminus of the first polynucleotide probe, the second polynucleotide probe or both. In some embodiments, at least one said modified purine nucleobase is no more than 1 nucleotides from the 3' terminus of the first polynucleotide probe, the second polynucleotide probe or both. In some embodiments, the modified purine nucleobase is the 3' terminal nucleotide of the first polynucleotide probe, the second polynucleotide probe or both.

In some embodiments, the first polynucleotide probe, the second polynucleotide probe or both comprise at least one of a detectable label, a quencher or a minor groove binder, or any combination thereof. In some embodiments, the first region overlaps the second region by one nucleotide base. In some embodiments, the 5' end of the first probe terminates with a group other than a nucleotide 5' phosphate group. In some embodiments, the 5' end of the first probe terminates with a nucleotide 5' hydroxyl group. In some embodiments, the 5' end of the second probe terminates with a group other than a nucleotide 5' phosphate group. In some embodiments, the 5' end of the second probe terminates with a nucleotide 5' hydroxyl group. In some embodiments, the 3' end of the second probe terminates with a group other than a nucleotide 3' hydroxyl group. In some embodiments, the 3' end of the second probe terminates with a nucleotide 3' phosphate group.

In some embodiments, the present teachings provide methods for detecting a target polynucleotide sequence comprising, (a) reacting a target-complementary strand with a second probe pair comprising (i) a third polynucleotide probe containing a sequence that is complementary to a first region in the target-complementary strand and (ii) a fourth polynucleotide probe containing a sequence that is complementary to a second region in the target-complementary strand, wherein the second region is located 5' to the first region and overlaps the first region by at least one nucleotide base, under conditions effective for the for the third and fourth probes to hybridize to the first and second regions in the target-complementary strand, respectively, forming a third hybridization complex, (b) cleaving the fourth probe in the second hybridization complex, to form a forth hybridization complex comprising the target-complementary strand, the third probe, and a first fragment of the forth probe having a 5' terminal nucleotide located immediately contiguous to a 3' terminal nucleotide of the third probe, (c) ligating the third probe to the hybridized fragment of the fourth probe to form a second ligated strand hybridized to the target-complementary strand, (d) denaturing the second ligated strand from the target-complementary strand, and (e) performing one or more additional cycles of steps (a) through (d), with the proviso that in the last cycle, step (d) is optionally omitted. In some embodiments, at least one of the third probe or the forth probe or both is a polynucleotide comprising at least one modified pyrimidine nucleobase comprising the structure

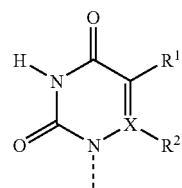

where X can be N or C, $R^1$ can be selected from —H, —F, —Cl, —Br, $C_1$-$C_6$ alkyl, $C_1$-$C_6$ substituted alkyl, $C_3$-$C_{10}$ aryl, $C_3$-$C_{10}$ substituted aryl, —$CF_3$, —$CF_2H$, —$CF_2CH_3$, —$CF_2CF_3$, —$CCl_3$, —CN, —CHO, —$CO_2R$, —$SO_3R$, —$PO_3RR$, —C(O)NRR, azido, and —$NO_2$, and $R^2$ can be selected from —H, —F, —Cl, —Br, $C_1$-$C_6$ alkyl, $C_1$-$C_6$ substituted alkyl, $C_3$-$C_{10}$ aryl, $C_3$-$C_{10}$ substituted aryl, —$CF_3$, —$CF_2H$, —$CF_2CH_3$, —$CF_2CF_3$, —$CCl_3$, —CN, —CHO, —$CO_2R$, —$SO_3R$, —$PO_3RR$, —C(O)NRR, azido, and —$NO_2$ where each R is independently —H, $C_1$-$C_6$ alkyl or $C_3$-$C_{10}$ aryl or alkylaryl, such that at least one of $R^1$ or $R^2$ is an electron withdrawing substituent or X is N, such that when X is N, $R^2$ is absent, and at least one said modified pyrimidine nucleobase is no more than 4 nucleotides from the 3' terminus of the polynucleotide. In some embodiments, the modified pyrimidine nucleobase can be selected from

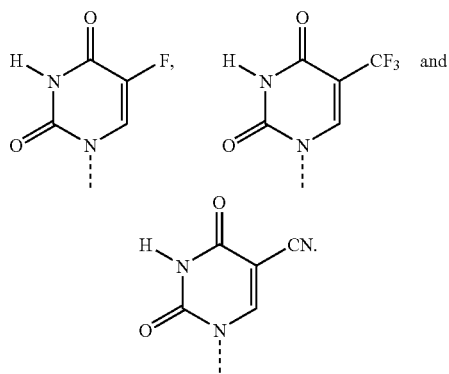

In some embodiments, at least one said modified purine nucleobase is no more than 2 nucleotides from the 3' terminus of the first polynucleotide probe, the second polynucleotide probe or both. In some embodiments, at least one said modified purine nucleobase is no more than 1 nucleotide from the 3' terminus of the first polynucleotide probe, the second polynucleotide probe or both. In some embodiments, said modified purine nucleobase can be the 3' terminal nucleotide of the first polynucleotide probe, the second polynucleotide probe or both. In some embodiments, the first polynucleotide probe, the second polynucleotide probe or both can comprise at least one of a detectable label, a quencher or a minor groove binder, or any combination thereof. In some embodiments, the 5' end of the third probe optionally terminates with a group other than a nucleotide 5' phosphate group. In some embodiments, the 5' end of the third probe optionally terminates with a nucleotide 5' hydroxyl group. In some embodiments, the 5' end of the fourth probe optionally terminates with a group other than a nucleotide 5' phosphate group. In some embodiments, the 5' end of the fourth probe optionally terminates with a nucleotide 5' hydroxyl group. In some embodiments, the 5' ends of the first, second, third and fourth probes optionally terminate with a group other than a nucleotide 5' phosphate group. In some embodiments, the 3' end of the fourth probe optionally terminates with a group other than a nucleotide 3' hydroxyl group. In some embodiments, the 3' end of the fourth probe optionally terminates with a nucleotide 3' phosphate group. In some embodiments, at least one of the probes contains a detectable label. In some embodiments, the label can be a fluorescent label. In some embodiments, the label can be a radiolabel. In some embodiments, the label can be a chemiluminescent label. In some embodiments, the label can be an enzyme. In some embodiments, at least one of the first probe and the third probe contains a detectable label. In some embodiments, each of the first probe and third probe contains a detectable label. In some embodiments, the detectable labels on the first probe and third probe are the same. In some embodiments, at least one of the second probe and the fourth probe contains a detectable label. In some embodiments, each of the second probe and the fourth probe contains a detectable label. In some embodiments, the second probe and fourth probe contain the same detectable label. In some embodiments, said cleaving produces a second fragment from the second probe which does not associate with the second hybridization complex, and the method further includes detecting said second fragment from the second probe. In some embodiments, said cleaving produces a second fragment from the forth probe which does not associate with the forth hybridization complex, and the method further includes detecting said second fragment from the forth probe. In some embodiments, at least one of the second probe and the fourth probe contains both (i) a fluorescent dye and (ii) a quencher dye which is capable of quenching fluorescence emission from the fluorescent dye when the fluorescent dye is subjected to fluorescence excitation energy, and said cleaving severs a covalent linkage between the fluorescent dye and the quencher dye in the second probe and/or fourth probe, thereby increasing an observable fluorescence signal from the fluorescent dye. In some embodiments, the second probe and the fourth probe each contain (i) a fluorescent dye and (ii) a quencher dye.

In some embodiments, methods of the present teachings for detecting target polynucleotide sequences method further include detecting both second fragments. In some embodiments, the second fragment comprises one or more contiguous nucleotides substantially non-complementary to the target strand. In some embodiments, the one or more contiguous nucleotides comprise 1 to 20 nucleotides.

In some embodiments, methods of the present teachings for detecting target polynucleotide sequences further include immobilizing the second fragment on a solid support. In some embodiments, methods of the present teachings for detecting target polynucleotide sequences further include subjecting the second fragment to electrophoresis. In some embodiments, methods of the present teachings for detecting target polynucleotide sequences further include detecting the second fragment by mass spectrometry. In some embodiments, methods of the present teachings for detecting target polynucleotide sequences comprise detecting the second fragment after the last cycle. In some embodiments, methods of the present teachings for detecting target polynucleotide sequences comprise detecting the second fragment during or after a plurality of cycles. In some embodiments, methods of the present teachings for detecting target polynucleotide sequences comprise detecting the second fragment during all of the cycles.

In some embodiments, methods of the present teachings for detecting target polynucleotide sequences further include detecting the first hybridization complex, the second hybridization complex, or both, after at least one cycle. In some embodiments, the method further includes detecting the third hybridization complex, the fourth hybridization complex, or both, after at least one cycle. In some embodiments, the method further includes detecting the first ligated strand, the second ligated strand, or both, after at least one cycle. In some embodiments, the detecting comprises an electrophoretic separation step.

In some embodiments, the present teachings provide for methods of fragment analysis comprising: i) annealing an oligonucleotide primer to a denatured DNA template such that, the oligonucleotide primer anneals to a complementary oligonucleotide sequence on a strand of the denatured DNA template to form a primer-template complex, ii) extending the primer portion of the primer-template complex in the presence of deoxyribonucleic acids and non-extendable ribonucleic acids to form DNA amplicon fragments, and iii) detecting the DNA amplicon fragments, where the oligonucleotide primer is an polynucleotide of the present teachings.

Scheme 1 below illustrates an exemplary polynucleotide comprising a plurality, (x), of nucleotides, "N", that may define a desired nucleotide sequence, wherein the subscripts 1, 2, 3 . . . x refer to the position of the nucleotide in the primer relative to the 3' end, and " . . . " indicates the possibility of one or more additional nucleotides between $N_x$ and $N_7$.

Scheme 1

Thus, $N_1$ is located at the 3' terminus of the exemplary polynucleotide, and can be referred to as the 3' terminal nucleotide of the exemplary polynucleotide. Similarly, $N_2$ is located at the second nucleotide position, and can be referred to as being 1 nucleotide from the 3' terminus. Similarly, $N_3$ is located at the third nucleotide position, and can be referred to as being 2 nucleotides from the 3' terminus. Similarly, $N_4$ is located at the fourth nucleotide position, and can be referred to as being 3 nucleotides from the 3' terminus. It is believed that the effect of reduced primer-dimer formation that results from incorporation of nucleobases of the present teachings into primers will decrease in primers having no nucleotide of the present teachings any nearer the 3'-terminus than about the $N_4$ position.

As used herein, the terms oligonucleotide, polynucleotide and nucleic acid are used interchangeably to refer to single- or double-stranded polymers of DNA, RNA or both including polymers containing modified or non-naturally occurring nucleotides. In addition, the terms oligonucleotide, polynucleotide and nucleic acid refer to any other type of polymer comprising a backbone and a plurality of nucleobases that can form a duplex with a complimentary polynucleotide strand by nucleobase-specific base-pairing including, but not limited to, peptide nucleic acids (PNAS) which are disclosed in, for example, Nielsen et al., *Science* 254:1497-1500 (1991), bicyclo DNA oligomers (Bolli et al., *Nucleic Acids Res.* 24:4660-4667 (1996)) and related structures.

In some embodiments, polynucleotides of the present teachings can comprise a backbone of naturally occurring sugar or glycosidic moieties, for example, β-D-ribofuranose. In addition, in some embodiments, modified nucleotides of the present teachings can comprise a backbone that includes one or more "sugar analogs". As used herein, the term "sugar analog" refers to analogs of the sugar ribose. Exemplary ribose sugar analogs include, but are not limited to, substituted or unsubstituted furanoses having more or fewer than 5 ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, —NRR or halogen groups, where each R is independently —H, ($C_1$-$C_6$) alkyl or ($C_3$-$C_{14}$) aryl. Examples of unsubstituted and substituted furanoses having 5 ring atoms include but are not limited to 2'-deoxyribose, 2'-($C_1$-$C_6$)-alkylribose, 2'-($C_1$-$C_6$)-alkoxyribose, 2'-($C_5$-$C_{14}$)-aryloxyribose, 2',3'-dideoxyribose, 2',3'-dideoxy-ribose, 2'-deoxy-3'-haloribose, 2'-deoxy-3'-fluororibose, 2'-deoxy-3'-chlororibose, 2'-de-oxy-3'-aminoribose, 2'-deoxy-3'-($C_1$-$C_6$)-alkylribose, 2'-deoxy-3'-($C_1$-$C_6$)-alkoxyribose, 2'-deoxy-3'-($C_5$-$C_{14}$)-aryloxyribose, 3'-($C_1$-$C_6$)-alkylribose-5'-triphosphate, 2'-deoxy-3'-($C_1$-$C_6$)-alkylribose-5'-triphosphate, 2'-deoxy-3'-($C_1$-$C_6$)-alkoxyribose-5'-triphosphate, 2'-deoxy-3'-($C_5$-$C_{14}$)-aryl-oxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-dide-hydroribose-5'-triphosphate. Further sugar analogs include but are not limited to, for example "locked nucleic acids" (LNAs), i.e., those that contain, for example, a methylene bridge between C-4' and an oxygen atom at C-2', such as

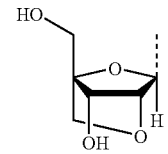

that are described in Wengel, et al. WO 99/14226, incorporated herein by reference, and Wengel J., *Acc. Chem. Res.*, 32:301-310 (1998).

In some embodiments, polynucleotides of the present teachings include those in which the phosphate backbone comprises one or more "phosphate analogs". The term "phosphate analog" refers to analogs of phosphate wherein the phosphorous atom is in the +5 oxidation state and one or more of the oxygen atoms are replaced with a non-oxygen moiety. Exemplary analogs include, but are not limited to, phosphorothioate, phosphorodithioate, phosphoroselenoate, phosphorodiselenoate, phosphoroanilothioate, phosphoranilidate, phosphoramidate, boronophosphates, and associated counterions, including but not limited to $H^+$, $NH_4^+$, $Na^+$, $Mg^{++}$ if such counterions are present. Polynucleotides of the present teachings containing phosphate analogs can comprise, for example, phosphorothioate linkages, methylphosphonates and/or phosphoroamidates (see, Chen et al., *Nucl Acids Res.*, 23:2662-2668 (1995)). Combinations of polynucleotide linkages are also within the scope of the present teachings.

In some embodiments, polynucleotides described herein can be incorporated into PNA and DNA/PNA chimeras. Including, peptide nucleic acids (PNAs, also known as polyamide nucleic acids), see, for example, Nielsen et al., *Science* 254:1497-1500 (1991). PNAs contain heterocyclic nucleobase units that are linked by a polyamide backbone instead of the sugar-phosphate backbone characteristic of DNA and RNA. PNAs are capable of hybridization to complementary DNA and RNA target sequences. Synthesis of PNA oligomers and reactive monomers used in the synthesis of PNA oligomers are described in, for example, U.S. Pat. Nos. 5,539,082; 5,714,331; 5,773,571; 5,736,336 and 5,766,855. Alternate approaches to PNA and DNA/PNA chimera synthesis and monomers for PNA synthesis have been summarized in, for example, Uhlmann, et al., *Angew. Chem. Int. Ed.* 37:2796-2823 (1998).

In some embodiments, polynucleotides of the present teachings can range in size from a few nucleotide monomers in length, e.g. from 5 to 80, to hundreds or thousands of nucleotide monomers in length. For example, polynucleotides of the present teachings can contain from 5 to 50 nucleotides, 5 to 30 nucleotides, or 5 to 20 nucleotides. When, in some embodiments, polynucleotides of the present teachings contain, for example, from 5 to 30 nucleotides, such a range includes all possible ranges of integers between 5 and 30, for example 5, 6, 7, 8, 9, 10, 11, 12, 13, 14, 15, 17, 18, 19, 20, 21, 22, 23, 24, 25, 26, 27, 28, 29 an 30 nucleotides in length. Whenever a polynucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxygaunosine, and T denotes thymidine, unless otherwise indicated. Additionally, whenever a polynucleotide of the present teachings is represented by a sequence of letters that includes an "X", it will be understood that the "X" denotes a variable nucleotide monomer, where "X" is a nucleotide monomer other than "A", "C", "G" or "T".

In some embodiments, polynucleotides of the present teachings can serve as primers in amplification reactions. As used herein, "primer" refers to a polynucleotide as defined herein having a 3' terminus that is extendable by addition of one or more nucleotide monomers or by ligation of a ligation probe.

In some embodiments, polynucleotides of the present teachings can comprise one or more nucleotides each independently comprising a modified nucleobase.

As used herein, the term "modified nucleobase" includes nucleobases that differ from the naturally-occurring bases (e.g. A, G, C, T and U) by addition and/or deletion of one or more functional groups, differences in the heterocyclic ring structure (i.e., substitution of carbon for a heteroatom, or vice versa), and/or attachment of one or more substituents capable of lowering the pKa of the N-3 imino proton of a pyrimidine nucleobase such that the $pK_a$ of the modified nucleobase is lower than the $pK_a$ of uridine. In some embodiments, the $pK_a$ of an imino proton on the modified nucleobase is $\leq 8$. In some embodiments, the $pK_a$ of an imino proton on the modified nucleobase is $\leq 7$. Examples of substituents capable of lowering the $pK_3$ of and imino proton suitable for use in connection with the present teachings include, but are not limited to, any substituent that is capable of lowering the $pK_a$ of the imino proton (e.g.—electron withdrawing) of the nucleobase such that the $pK_a$ of the modified nucleobase is lower than the $pK_a$ of uridine. Examples of such substituents include but are not limited to substituted lower alkyl, substituted aryl —CN, —CF$_3$, —CHF$_2$, —CCl$_3$, —CO$_2$R, —CONR$_2$, —NO$_2$, halogen, fluorine, chlorine and bromine where each R is independently —H, $C_1$-$C_6$ alkyl or $C_3$-$C_{10}$ aryl or alkylaryl.

In some embodiments, modified nucleobases for use with the present teachings include modified pyrimidine nucleobases having the structure

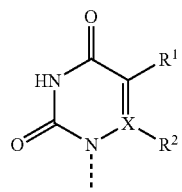

wherein X can be N or C, $R_1$ is selected from halogen, fluorine, chlorine, bromine, $C_1$-$C_6$ alkyl, substituted $C_1$-$C_6$ alkyl, $C_3$-$C_{10}$ aryl, substituted $C_3$-$C_{10}$ aryl, —CF$_3$, —CF$_2$H, —CF$_2$CH$_3$, —CF$_2$CF$_3$, —CCl$_3$, —CN, —CHO, —CO$_2$R, —SO$_3$R, —PO$_3$R$_2$, —C(O)NR$_2$, azido, and —NO$_2$, and $R_2$ is selected from halogen, fluorine, chlorine, bromine, $C_1$-$C_6$ alkyl, substituted $C_1$-$C_6$ alkyl, $C_3$-$C_{10}$ aryl, substituted $C_3$-$C_{10}$ aryl, —CF$_3$, —CF$_2$H, —CF$_2$CH$_3$, —CF$_2$CF$_3$, —CCl$_3$, —CN, —CHO, —CO$_2$R, —SO$_3$R, —PO$_3$R$_2$, —C(O)NR$_2$, azido, and —NO$_2$ where each R is independently —H, $C_1$-$C_6$ alkyl or $C_3$-$C_{10}$ aryl or alkylaryl, for example, benzyl.

As used herein, "alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl (methanyl); ethyls such as ethanyl, ethenyl, ethynyl; propyls such as propan-1-yl, propan-2-yl (isopropyl), cyclopropan-1-yl, prop-1-en-1-yl, prop-1-en-2-yl, prop-2-en-1-yl, cycloprop-1-en-1-yl; cyclo-prop-2-en-1-yl, prop-1-yn-1-yl, prop-2-yn-1-yl, etc.; butyls such as butan-1-yl, butan-2-yl (sec-butyl), 2-methyl-propan-1-yl (isobutyl), 2-methyl-propan-2-yl (t-butyl), cyclobutan-1-yl, but-1-en-1-yl, but-1-en-2-yl, 2-methyl-prop-1-en-1-yl, but-2-en-1-yl but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Furthermore, cyclic alkyl groups may optionally have one or more ring carbon atoms substituted by a heteroatom selected from O, S or N. Examples of such "heteroalkyl" groups include, but are not limited to morpholine, pyran and the like.

As used herein, "aryl" refers to a monovalent aromatic hydrocarbon radical derived by the removal of one hydrogen atom from a single carbon atom of an aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryl group is ($C_5$-$C_{20}$) aryl or ($C_5$-$C_{10}$) aryl. Further aryl groups are phenyl ($C_6$ aryl) and naphthyl ($C_{10}$ aryl).

As used herein, "substituted" as in "substituted alkyl", "substituted aryl" or "substituted alkylaryl", means that the alkyl, aryl, amine, cyclic alkyl or phenyl moiety is substituted by one or more substituents. Such substituents include, but are not limited to, —F, —Cl, —Br, —CF$_3$, —CCl$_3$, —CN, —CHO, —CO$_2$R, —SO$_3$R, —PO$_3$RR, —C(O)NRR and —NO$_2$ where each R is independently —H, $C_1$-$C_6$ alkyl, $C_3$-$C_{10}$ aryl or alkylaryl.

In some embodiments, modified nucleobases for use in the present teachings include, but are not limited to, 5-cyanouracil (5-CN-U), 5-fluorouracil (5-F-U) and 5-trifluormethyluracil (5-CF$_3$-U).

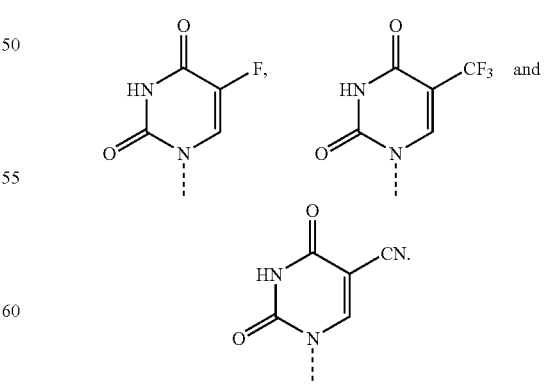

Examples of nucleosides/tides including an electron withdrawing substituent as described above include, but are not limited to, 5-cyano-2'-deoxyuridine, 5-fluoro-2'-deoxyuridine and 5-trifluormethyl-2'-deoxyuridine, 5-cyanouridine, 5-fluorouridine and 5-trifluoromethyluridine.

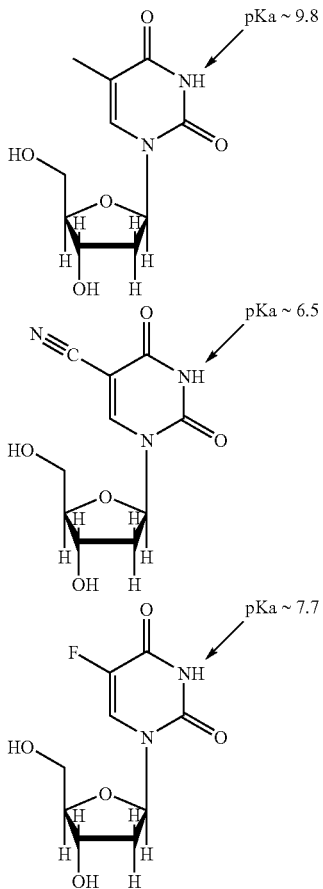

The pK$_a$ value of the N-3 imino proton of 5-cyano-2'-deoxyuridine and 5-fluoro-2'-deoxyuridine have been reported in the literature as being about 6.50 and about 7.7 respectively (Ishikawa, R. et al., *Magnetic Resonance in Chemistry*, v. 39, S159-S165 (2001)). In contrast, the pK$_a$ of the imino proton in uridine is ~9.8. 5-cyano-2'-deoxyuridine can be prepared according to published literature procedures (see, for example, Hampton, et al., *J. Med. Chem.*, v. 22 (6), 621-631 (1979)).

It will be understood that substituted for use in connection with the present teachings are well known in the art. Further examples of modified nucleobases and nucleosides/tides and the preparation thereof, having various X, R$^1$ and R$^2$ substitution patterns for use in connection with the present teachings include, but are not limited to, those described in, Felczak, K., et al. *J. Med. Chem.*, v. 39, 1720-1728 (1996), Mertes, M., et al., *J. Med. Chem.*, v. 9, 876-81 (1966), Mertes, M., et al., *J. Med. Chem.*, 619 (1963), Khomov-Borisov, N., et al., *Zhurnal Obshchei Khimii*, v. 27, 2518-21 (1957), Giner-Sorolla, A., *J. Am. Chem. Soc.*, v. 80, 5744-52 (1958), Wempen, I., et al., *J. Med. Chem.*, 207-9 (1964), Greenbaum, S., et al. *J. Am. Chem. Soc.*, v. 76, 2899-2902 (1954), Vissen, B., et al., *J. Biol. Chem.*, v. 171, 377-81 (1947) and Asburn, W., *J. Org. Chem.*, 31(7), 2215-19 (1966), Honjo, M., et al., *Chem. & Pharm. Bull.*, 35(8), 3227-34 (1987), Ueda, T., et al., *Chem. & Pharm. Bull.*, 23(11), 2614-19 (1975), Tanaka, H., et al., *Tetrahedron*, 38(17), 2635-42 (1982), Groziak, M. P., et al., *J. Org. Chem.*, 58(15), 4054-60 (1993), Tanaka, H., et al., *Tetrahedron*, 41(5), 861-6 (1985), De Zeeuw, J. R., et al., *J. of Antibiotics*, 22(8), 386-7 (1969), Beckvermit, J. T., et al., U.S. Pat. No. 6,020,483, Matsuda, A., et al., *Bioorg. & Med. Chem. Letters*, 3(12), 2751-4 (1993), Giziewicz, J., et al., *J. Org. Chem.*, 64(6), 2149-51 (1999), Guemiou, V. et al., *Nucleosides, Nucleotides & Nucleic Acids*, 22(5-8), 1073-75 (2003), Barr, P. J., et al. *Tetrahedron*, 36(9), 1269-73, Kampf, A., et al., *J. Med. Chem.*, 19(7), 909-15 (1976), Matulic-Adamic, J., et al., *J. Chem. Soc., Chem. Comm.*, v. 21, 1535-6 (1985), Haginoya, N., et al., *Bioconjugate Chem.*, 8(3), 271-80 (1997), Kalman, T., et al., *Nucleic Acid Chem*, v. 4, 84-6 (1991), Cody, V., et al. *Nucleosides & Nucleotides*, 4(5), 587-94 (1985), and references cited therein.

Further examples of commercially available and non-commercially available nucleobases and nucleosides/tides for use in connection with the present teachings and methods of making them can be found in a variety of databases that are known in the art, including Scifinder® Scholar, Chemical Abstracts®, and the like. It will be understood that further nucleosides and nucleotides for use in connection with the present teachings will be readily accessible to those of skill in the art by chemical synthetic methods well known in the art in combination with or independent of the teachings provided herein and in the references cited above.

All tautomeric forms of naturally occurring bases, modified bases and base analogues may be included in oligonucleotides of the present teachings.

Accordingly, polynucleotides having any combination of normal bases, modified pyrimidine nucleobases, universal bases, sugar modifications, or backbone modifications of DNA, PNA or DNA/PNA chimeras are within the scope of the present teachings.

In some embodiments polynucleotides of the present teachings can be conjugated to at least one detectable label, nonfluorescent quencher and/or at least one stabilizing moiety. In some embodiments polynucleotides of the present teachings that are conjugated to at least one detectable label, nonfluorescent quencher and/or at least one stabilizing moiety can serve as probes or primers in amplification reactions.

The term "detectable label" refers to any moiety that, when attached to polynucleotides of the present teachings, render such polynucleotides detectable using known detection means. Exemplary detectable labels include, but are not limited to, fluorophores, chromophores, radioisotopes, spin-labels, enzyme labels or chemiluminescent labels that allow for direct detection of a labeled compound by a suitable detector, or a binding pair, for example, a ligand, such as an antigen or biotin, that can bind specifically with high affinity to a detectable anti-ligand, such as a labeled antibody or avidin. In some embodiments the labels can be fluorescent dyes, such as fluorescein or rhodamine dyes or fluorescent dye pairs, such as FRET dyes.

In some embodiments, polynucleotides of the present teachings can comprise one or more "nonfluorescent quencher" moieties. As used herein, "nonfluorescent quencher" includes but is not limited to, for example, particular azo dyes (such as DABCYL or DABSYL dyes and their structural analogs), triarylmethane dyes such as malachite green or phenol red, 4',5'-diether substituted fluoresceins (U.S. Pat. No. 4,318,846), asymmetric cyanine dye quenchers (see, Lee et al., U.S. Pat. No. 6,080,868 and Lee, et al., U.S. Pat. No. 6,348,596), or nonfluorescent derivatives of 3- and/or 6-amino xanthene that is substituted at one or more amino nitrogen atoms by an aromatic or heteroaromatic ring system (Haugland, et al., U.S. Pat. No. 6,399,392).

"Nonfluorescent", as used herein, indicates that the fluorescence efficiency of the quenching moiety in an assay solution as described for any of the methods herein is less than or equal to 5 percent emission at emission-$\lambda_{max}$. In some embodiments, less than or equal to 1 percent emission at emission-$\lambda_{max}$. In some embodiments of the present teachings, the covalently bound quenching moiety exhibits a quantum yield of less than about 0.1 percent emission at emission-$\lambda_{max}$. In some embodiments, less than about 0.01 percent emission at emission-$\lambda_{max}$.

In some embodiments, polynucleotides of the present teachings can be conjugated to at least one "stabilizing moiety". As used herein, the term "stabilizing moiety" refers to moieties that include but are not limited to minor groove binder (MGB) moieties. A variety of suitable minor groove binders have been described in the literature. See, for example, Kutyavin, et al. U.S. Pat. No. 5,801,155; Wemmer, D. E., and Dervan P. B., Current Opinon in Structural Biology, 7:355-361 (1997); Walker, W. L., Kopka, J. L. and Goodsell, D. S., Biopolymers, 44:323-334 (1997); Zimmer, C & Wahnert, U. Prog. Biophys. Molec. Bio. 47:31-112 (1986) and Reddy, B. S. P., Dondhi, S. M., and Lown, J. W., Pharmacol. Therap., 84:1-111 (1999).

Suitable methods for attaching MGBs (as well as reporter groups such as fluorophores and quenchers described above) through linkers to polynucleotides are described in, for example, U.S. Pat. Nos. 5,512,677; 5,419,966; 5,696,251; 5,585,481; 5,942,610 and 5,736,626. Minor groove binders include, for example, the trimer of 3-carbamoyl-1,2-dihydro-(3-H7)-pyrrolo[3,2-e]indole-7-carboxylate ($CDPI_3$) and the pentamer of N-methylpyrrole-4-carbox-2-amide ($MPC_5$). Additional MGB moieties are disclosed in U.S. Pat. No. 5,801,155. In certain embodiments, the MGBs can have attached water solubility-enhancing groups (e.g., sugars or amino acids).

Polynucleotides of the present teachings can find use as primers and/or probes in, for example, polynucleotide chain extension or ligation reactions. As used herein, "chain extension reaction" refers to primer extension reactions in which at least one polynucleotide of the present teachings (e.g.—as primers or ligation probes) can be annealed to at least one DNA template strand. After the step of annealing in a polynucleotide chain extension reaction, the primer can then be extended by at least one nucleotide to form an amplicon or extension product. Alternatively, after the step of annealing in a polynucleotide chain extension reaction, the primer can be ligated to a second ligation probe to form a ligation product. The present teachings encompass all possible chain extension reactions including, but not limited to, polymerase chain reaction (PCR), nested PCR, asynchronous PCR, real time PCR, TaqMan assays, DNA sequencing, cycled DNA sequencing, oligonucleotide ligation assay (OLA), and fragment analysis, described in, for example, *The PCR Technique: DNA Sequencing II*, Eaton Publishing Co. (1997), *Genome Analysis, A Laboratory Manual Volume 1: Analyzing DNA*, Birren, B., Green, E., Klapholz, S., Myers, R. M. and Roskams, J. Eds., Cold Spring Harbor Laboratory Press (1997), Innis, M. et al., *PCR Protocols: A Guide to Methods and Applications*, Academic Press (1989), Chen, C. et al., U.S. Patent Application Pub. No. 2003/0207266A1, Erlich, et al., U.S. Pat. No. 5,314,809, U.S. Pat. No. 6,221,606 and Bi, W., et al., U.S. Pat. No. 6,511,810. Oligonucleotides of the present teachings can be used in any of the above primer extension reactions as either primers or probes where each is appropriate.

In some embodiments, the present teachings provide for methods of primer extension comprising, annealing a polynucleotide primer to a denatured DNA template such that, the polynucleotide primer anneals to a complementary polynucleotide sequence on a strand of the denatured DNA template to form a primer-template complex, and extending the primer portion of the primer-template complex to form a double stranded amplicon, wherein the polynucleotide primer is a primer according to the present teachings.

In some embodiments, the present teachings provide for methods of primer extension comprising, after the step of extending, denaturing the double stranded amplicon. In some embodiments, the steps of annealing, extending and denaturing can be repeated at least one time. In some embodiments, the steps of annealing, extending and denaturing can be repeated at least 10 times. In some embodiments, the steps of annealing, extending and denaturing can be repeated at least 20 times. In some embodiments, the steps of annealing, extending and denaturing can be repeated at least 30 times. In some embodiments, the steps of annealing, extending and denaturing can be repeated at least 40 times.

In some embodiments, the present teachings provide for a method of primer extension comprising i) annealing a first polynucleotide primer and a second polynucleotide primer to a first and second strand of a denatured DNA template such that, the first polynucleotide primer anneals to a complementary oligonucleotide sequence on the first strand of the denatured DNA template and the second polynucleotide primer anneals to a complementary oligonucleotide sequence on the second strand of the denatured DNA template to form a first and a second primer-template complex, and ii) extending the primer portion of at least one of the first and second primer-template complex to form double stranded DNA amplicon, wherein at least one of the first polynucleotide primer or the second polynucleotide primer can be a polynucleotide of the present teachings. In some embodiments, prior to the step of annealing, the method can include the step of forming a mixture comprising a first polynucleotide primer, a second polynucleotide primer, a DNA template, and other primer extension reagents, including, for example buffers and polymerases. In some embodiments, polymerases for use in the present teachings can comprise at least one thermostable polymerase, including, but not limited to, Taq, Pfu, Vent, Deep Vent, Pwo, UITma, and Tth polymerase and enzymatically active mutants and variants thereof. Such polymerases are well known and/or are commercially available. Descriptions of polymerases can be found, among other places, at the world wide web URL: the-scientist.library.upenn.edu/yr1998/jan/profile1_980105.html.

In some embodiments, after the step of forming but prior to the step of annealing, the method can include the step of denaturing the DNA template to form a first strand of denatured DNA template and a second denatured DNA template. In some embodiments, after the step of extending, denaturing the double stranded DNA amplicon. In some embodiments, the steps of annealing, extending and denaturing the double stranded DNA amplicon can be repeated from 1-100 times. In some embodiments, the steps of annealing, extending and denaturing the double stranded DNA amplicon can be repeated from 10-100 times. In some embodiments, the steps of annealing, extending and denaturing the double stranded DNA amplicon can be repeated from 20-100 times. In some embodiments, the steps of annealing, extending and denaturing the double stranded DNA amplicon can be repeated from 30-100 times. In some embodiments, the steps of annealing, extending and denaturing can be repeated at least one time. In some embodiments, the steps of annealing, extending and denaturing can be repeated at least 10 times. In some embodiments, the steps of annealing, extending and denaturing can be repeated at least 20 times. In some embodiments, the steps of annealing, extending and denaturing can be repeated at least 30 times. In some embodiments, the steps of annealing, extending and denaturing can be repeated at least 40 times.

In some embodiments, the present teachings provide for methods of primer extension comprising, prior to the step of extending the primer portion, annealing a polynucleotide probe to a first or second strand of a denatured DNA template such that, the polynucleotide probe anneals to a complementary polynucleotide sequence on the first strand of the denatured DNA template and/or the polynucleotide probe anneals to a complementary oligonucleotide sequence on the second strand of the denatured DNA template. In some embodiments, the polynucleotide probe comprises at least one detectable label. In some embodiments, the polynucleotide probe further comprises at least one of a quencher, a minor groove binder or both. In some embodiments, the polynucleotide probe can be a polynucleotide of the present teachings.

In some embodiments, the present teachings provide "fragment analysis" or "genetic analysis" methods, wherein labeled polynucleotide fragments can be generated through template-directed enzymatic synthesis using labeled primers or nucleotides, the fragments can be subjected to a size-dependent separation process, e.g., electrophoresis or chromatography; and, the separated fragments can be detected subsequent to the separation, e.g., by laser-induced fluorescence. In some embodiments, multiple classes of polynucleotides are separated simultaneously and the different classes are distinguished by spectrally resolvable labels.

In some embodiments, the present teachings provide a method of fragment analysis in which fragment classes can be identified and defined in terms of terminal nucleotides so that a correspondence is established between the four possible terminal bases and the members of a set of spectrally resolvable dyes. Such sets are readily assembled from the fluorescent dyes known in the art by measuring emission and absorption bandwidths using commercially available spectrophotometers. In some embodiments, fragment classes are formed through chain termination methods of DNA sequencing, i.e., dideoxy DNA sequencing, or Sanger-type sequencing.

Sanger-type sequencing involves the synthesis of a DNA strand by a DNA polymerase in vitro using a single-stranded or double-stranded DNA template whose sequence is to be determined. Synthesis is initiated at a defined site based on where an oligonucleotide primer anneals to the template. The synthesis reaction is terminated by incorporation of a nucleotide analog that will not support continued DNA elongation. Exemplary chain-terminating nucleotide analogs include the 2',3'-dideoxynucleoside 5'-triphosphates (ddNTPs) which lack the 3'-OH group necessary for 3' to 5' DNA chain elongation. When proper proportions of dNTPs (2'-deoxynucleoside 5'-triphosphates) and one of the four ddNTPs are used, enzyme-catalyzed polymerization will be terminated in a fraction of the population of chains at each site where the ddNTP is incorporated. If labeled primers or labeled ddNTPs are used for each reaction, the sequence information can be detected by fluorescence after separation by high-resolution electrophoresis. In the chain termination method, dyes of the invention can be attached to either sequencing primers or dideoxynucleotides. In the method, fluorescent dye molecules can be linked to a complementary functionality at, for example, the 5'-terminus of a primer, e.g. following the teaching in Fung, et al., U.S. Pat. No. 4,757,141; on the nucleobase of a primer; or on the nucleobase of a dideoxynucleotide, e.g. via the alkynylamino linking groups disclosed by Hobbs et al, in European Patent Application No. 87305844.0, and Hobbs et al., *J. Org. Chem.*, 54: 3420 (1989) incorporated herein by reference.

In some embodiments, labeled polynucleotides can be preferably separated by electrophoretic procedures as disclosed in, for example, Rickwood and Hames, Eds., *Gel Electrophoresis of Nucleic Acids: A Practical Approach*, IRL Press Limited, London, 1981; Osterman, *Methods of Protein and Nucleic Acid Research*, Vol. 1 Springer-Verlag, Berlin, 1984; or U.S. Pat. Nos. 5,374,527, 5,624,800 and/or 5,552,028. In some embodiments, the type of electrophoretic matrix can be crosslinked or uncrosslinked polyacrylamide having a concentration (weight to volume) of between about 2-20 weight percent. In some embodiments, the polyacrylamide concentration is between about 4-8 percent. In some embodiments, for example in DNA sequencing, the electrophoresis matrix can include a denaturing agent, e.g., urea, formamide, and the like. Detailed procedures for constructing such matrices are given by, for example, Maniatis et al., "Fractionation of Low Molecular Weight DNA and RNA in Polyacrylamide Gels Containing 98% Formamide or 7 M Urea," in *Methods in Enzymology*, 65: 299-305 (1980); Maniatis et al., "Chain Length Determination of Small Double- and Single-Stranded DNA Molecules by Polyacrylamide Gel Electrophoresis," *Biochemistry*, 14: 3787-3794 (1975); Maniatis et al., *Molecular Cloning: A Laboratory Manual*, Cold Spring Harbor Laboratory, New York, pgs. 179-185 (1982); and *ABI PRISM™ 377 DNA Sequencer User's Manual*, Rev. A, January 1995, Chapter 2 (Applied Biosystems, Foster City, Calif.). It will be understood that optimal electrophoresis conditions, for example, polymer concentration, pH, temperature, and concentration of denaturing agent, employed in a particular separation depends on many factors, including the size range of the nucleic acids to be separated, their base compositions, whether they are single stranded or double stranded, and the nature of the classes for which information is sought by electrophoresis.

Subsequent to electrophoretic separation, labeled polynucleotides can be detected by, for example, measuring the fluorescence emission from a dye on the labeled polynucleotides. To perform such detection, the labeled polynucleotides are illuminated by standard means, such as high intensity mercury vapor lamps, lasers, or the like. In some embodiments, the illumination means is a laser having an illumination beam at a wavelength above about 600 nm. In some embodiments, the dye-polynucleotides are illuminated by laser light generated by a He—Ne gas laser or a solid-state diode laser. After illumination, fluorescence intensity of the labeled polynucleotide can be measured by a light-sensitive detector, such as a photomultiplier tube, charged coupled device, or the like. Exemplary electrophoresis detection systems are described elsewhere, e.g., U.S. Pat. Nos. 5,543,026; 5,274,240; 4,879,012; 5,091,652 and 4,811,218.

In some embodiments, the present teachings provide for a method of fragment analysis comprising, annealing an polynucleotide primer to a denatured DNA template, such that the polynucleotide primer anneals to a complementary polynucleotide sequence on a strand of the denatured DNA template to form a primer-template complex, extending the primer portion of the primer-template complex in the presence of extendable nucleotide triphosphates and non-extendable nucleotide triphosphates to form DNA amplicon fragments and detecting the DNA amplicon fragments. In some embodiments, the polynucleotide primer can be an oligonucleotide of the present teachings. Further embodiments of fragment analysis methods in accordance with the present teachings can be found in, for example, U.S. Pat. No. 6,221,606 incorporated herein by reference.

As used herein, "ligation reaction" refers to reactions in which allele specific ligation probes are annealed to at least one DNA template strand to form a probe-template complex.

After the step of annealing, a covalent bond is then formed between the probe and the second oligonucleotide fragment by a ligation agent to form a ligation product. A ligation agent according to the present invention may comprise any number of enzymatic or chemical (i.e., non-enzymatic) agents. For example, ligase is an enzymatic ligation agent that, under appropriate conditions, forms phosphodiester bonds between the 3'-OH and the 5'-phosphate of adjacent polynucleotides. Temperature-sensitive ligases, include, but are not limited to, bacteriophage T4 ligase, bacteriophage T7 ligase, and *E. coli* ligase. Thermostable ligases include, but are not limited to, Taq ligase, Tth ligase, and Pfu ligase. Thermostable ligase may be obtained from thermophilic or hyperthermophilic organisms, including but not limited to, prokaryotic, eucaryotic, or archael organisms. Some RNA ligases may also be employed in the methods of the invention.

Chemical ligation-agents include, without limitation, activating, condensing, and reducing agents, such as carbodiimide, cyanogen: bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the invention. Detailed protocols for chemical ligation methods and descriptions of appropriate reactive groups can be found, among other places, in Xu et al., Nucleic Acid Res., 27:875-81 (1999); Gryaznov and Letsinger, Nucleic Acid Res. 21:1403-08 (1993); Gryaznov et al., Nucleic Acid Res. 22:2366-69 (1994); Kanaya and Yanagawa, Biochemistry 25:7423-30 (1986); Luebke and Dervan, Nucleic Acids Res. 20:3005-09 (1992); Sievers and von Kiedrowski, Nature 369:221-24 (1994); Liu and Taylor, Nucleic Acids Res. 26:3300-04 (1999); Wang and Kool, Nucleic Acids Res. 22:2326-33 (1994); Purmal et al., Nucleic Acids Res. 20:3713-19 (1992); Ashley and Kushlan, Biochemistry 30:2927-33 (1991); Chu and Orgel, Nucleic Acids Res. 16:3671-91 (1988); Sokolova et al., FEBS Letters 232:153-55 (1988); Naylor and Gilham, Biochemistry 5:2722-28 (1966); U.S. Pat. No. 5,476,930; and Royer, EP 324616B1). In some embodiments, the ligation agent is an "activating" or reducing agent. It will be appreciated that if chemical ligation is used, the 3' end of the first probe and the 5' end of the second probe should include appropriate reactive groups to facilitate the ligation.

In some embodiments, the present teachings provide methods of oligonucleotide ligation comprising, i) forming a complex comprising a first and a second polynucleotide strand annealed to a DNA template such that, the first polynucleotide strand anneals to a first complementary polynucleotide sequence on the strand of the denatured DNA template and the second polynucleotide strand anneals to a second complementary polynucleotide sequence on the strand of the denatured DNA template, wherein the second complementary polynucleotide sequence on the strand of the denatured DNA template is located 5' to the first complementary polynucleotide sequence on the strand of the denatured DNA template, and ii) forming a stable covalent bond between the first and second polynucleotide strands, wherein at least one of the first polynucleotide strand or the second polynucleotide strand is a polynucleotide of the present teachings.

In some embodiments, the present teachings provide a method of oligonucleotide ligation comprising, annealing a first oligonucleotide to a strand of a denatured DNA template such that, the first oligonucleotide anneals to a complementary oligonucleotide sequence on the strand of the denatured DNA template to form a first oligonucleotide-template complex, annealing a second oligonucleotide to an oligonucleotide sequence on the first oligonucleotide-template complex that is complementary to the second oligonucleotide to form a second oligonucleotide-template complex, wherein the second oligonucleotide anneals to the first oligonucleotide-template complex so that the 3'-terminus of the first oligonucleotide and the 5'-terminus of the second oligonucleotide are associated with adjacent nucleotides of the denatured DNA template, and forming a stable covalent bond between the 3'-terminus of the first oligonucleotide and the 5'-terminus of the second oligonucleotide. In some embodiments, at least one of the first oligonucleotide or the second oligonucleotide can be an oligonucleotide of the present teachings.

In some embodiments, the present teachings provide for a method for detecting a target polynucleotide sequence comprising (a) reacting a target polynucleotide strand and a target-complementary strand with a first probe pair and a second probe pair, the first probe pair comprising (i) a first polynucleotide probe containing a sequence that is complementary to a first target region in the target strand and (ii) a second polynucleotide probe comprising a sequence that is complementary to a second target region in the target strand, wherein the second region is located 5' to the first region and overlaps the first region by at least one nucleotide base, and the second probe pair comprising (i) a third polynucleotide probe containing a sequence that is complementary to a first region in the target-complementary strand and (ii) a fourth polynucleotide probe containing a sequence that is complementary to a second region in the target-complementary strand, wherein the second region is located 5' to the first region and overlaps the first region by at least one nucleotide base, under conditions effective for the first and second probes to hybridize to the first and second regions in the target strand, respectively, forming a first hybridization complex, and for the third and fourth probes to hybridize to the first and second regions in the target-complementary strand, respectively, forming a second hybridization complex, (b) cleaving the second probe in the first hybridization complex, and the fourth probe in the second hybridization complex, to form (i) a third hybridization complex comprising the target strand, the first probe, and a first fragment of the second probe having a 5' terminal nucleotide located immediately contiguous to a 3' terminal nucleotide of the first probe, and (ii) a fourth hybridization complex comprising the target-complementary strand, the third probe, and a first fragment of the fourth probe having a 5' terminal nucleotide located immediately contiguous to a 3' terminal nucleotide of the third probe, (c) ligating the first probe to the hybridized fragment of the second probe to form a first ligated strand hybridized to the target strand, and ligating the third probe to the fragment of the fourth probe to form a second ligated strand hybridized to the target-complementary strand, (d) denaturing the first ligated strand from the target strand and the second ligated strand from the target-complementary strand, and (e) performing one or more additional cycles of steps (a) through (d), with the proviso that in the last cycle, step (d) is optionally omitted.

In some embodiments, the first region can overlap the second region by one nucleotide base. In some embodiments, the 5' ends of the first and third probes can terminate with a group other than a nucleotide 5' phosphate group. In some embodiments, the 5' ends of the first and third probes can terminate with a nucleotide 5' hydroxyl group. In some embodiments, the 5' ends of the second and fourth probes can terminate with a group other than a nucleotide 5' phosphate group. In some embodiments, the 5' ends of the second and fourth probes can terminate with a nucleotide 5' hydroxyl group. In some embodiments, the 5' ends of the first, second, third and fourth probes can each independently terminate with a group other than a nucleotide 5' phosphate group. In some embodiments, the 3' ends of the second and fourth probes can each independently terminate with a group other than a nucleotide 3' hydroxyl group. In some embodiments, the 3' ends of the second and fourth probes can terminate with a nucleotide 3' phosphate group.

In some embodiments, at least one of the probes can contain a detectable label. In some embodiments, the label can be a fluorescent label. In some embodiments, the label can be a radiolabel. In some embodiments, the label can be a chemiluminescent label. In some embodiments, the label can be an enzyme. In some embodiments, at least one of the first probe and the third probe can contain a detectable label. In some embodiments, each of the first probe and third probe can contain a detectable label. In some embodiments, the detectable labels on the first probe and third probe can be the same. In some embodiments, at least one of the second probe and the fourth probe; can contain a detectable label. In some embodiments, each of the second probe and the fourth probe contains a detectable label. In some embodiments, the second probe and fourth probe can contain the same detectable label.

In some embodiments, the step of cleaving produces a second fragment from the second probe which does not associate with the third hybridization complex, and the method further includes detecting said second fragment.

In some embodiments, at least one of the second probe and the fourth probe contains both (i) a fluorescent dye and (ii) a quencher dye which is capable of quenching fluorescence emission from the fluorescent dye when the fluorescent dye is subjected to fluorescence excitation energy, and said cleaving severs a covalent linkage between the fluorescent dye and the quencher dye in the second probe and/or fourth probe, thereby increasing an observable fluorescence signal from the fluorescent dye. In some embodiments, the second probe and the fourth probe can each contain (i) a fluorescent dye and (ii) a quencher dye.

In some embodiments, the step of cleaving further produces a second fragment from the fourth probe that does not associate with the fourth hybridization complex, and the method further includes detecting both second fragments. In some embodiments, the second fragment comprises one or more contiguous nucleotides that are substantially non-complementary to the target strand. In some embodiments, one or more contiguous nucleotides comprise 1 to 20 nucleotides.

In some embodiments, the method further includes immobilizing the second fragment on a solid support. In some embodiments, the method further includes subjecting the second fragment to electrophoresis. In some embodiments, the method further includes detecting the second fragment by mass spectrometry. In some embodiments, the method further comprises detecting the second fragment after the last cycle. In some embodiments, the method further comprises detecting the second fragment during or after a plurality of cycles. In some embodiments, the method further comprises detecting the second fragment during all of the cycles. In some embodiments, the method further includes detecting the first hybridization complex, the second hybridization complex, or both, after at least one cycle. In some embodiments, the method further includes detecting the third hybridization complex, the fourth hybridization complex, or both, after at least one cycle. In some embodiments, the method further includes detecting the first ligated strand, the second ligated strand, or both, after at least one cycle. In some embodiments, said detecting comprises an electrophoretic separation step.

Further embodiments of the ligation method for detecting a target polynucleotide can be found in Bi, W., et al., U.S. Pat. No. 6,511,810 incorporated herein by reference in its entirety.

EXAMPLES

Materials and Methods

Unless otherwise indicated, all synthesis reactions were carried out in oven or flame dried glassware, under an atmosphere of Argon. Tetrahydrofuran (THF) and methylene chloride ($CH_2Cl_2$) were distilled from calcium hydride ($CaH_2$) under Argon. Unless otherwise indicated, all other solvents were used as received from the distributor. Thin layer chromatography (TLC) was performed on 1 mm silica gel plates purchased from. Sigma-Aldrich (Milwaukee, Wis.) and visualized with UV light (Spectroline; model ENF-240C) or stained with $KMnO_4$ or phosphomolybdic acid. Flash column chromatography was performed using silica gel with an average particle size of 40 μm purchased from Sigma-Aldrich (Milwaukee, Wis.). 5-Cyano-2'-deoxyuridine was synthesized according to Hampton, et al., *J. Med. Chem.*, v. 22 (6), 621-631 (1979). 5-Fluoro-2'-deoxyuridine CPG support was purchased from ChemGenes Corp. (Wilmington, Mass.). Non-derivitized CPG support was obtained from Applied Biosystems Inc (P/N 360139, Foster City, Calif.). Unless otherwise indicated, all other reagents were purchased from Sigma-Aldrich. Unless otherwise indicated, automated DNA synthesis was carried out on an ABI 394 DNA synthesizer at a 0.2 μmol scale following the standard protocol. Oligonucleotides were purified by reversed phase HPLC on an Agilent 1100 HPLC system. ESI-TOF mass spectra were recorded on a Mariner mass spectrometer (Applied Biosystems, Foster City). The purity of synthesized oligo-nucleotides was checked by capillary electrophoresis (CE) on an Agilent CE system.

Oligonucleotide Synthesis

5-Cyano-2'-deoxyuridine CPG and
5-trifluoromethyl-2'-deoxyuridine CPG

5-Cyano-2'-deoxyuridine CPG and 5-trifluoromethyl-2'-deoxyunridine CPG were synthesized according Scheme 1.

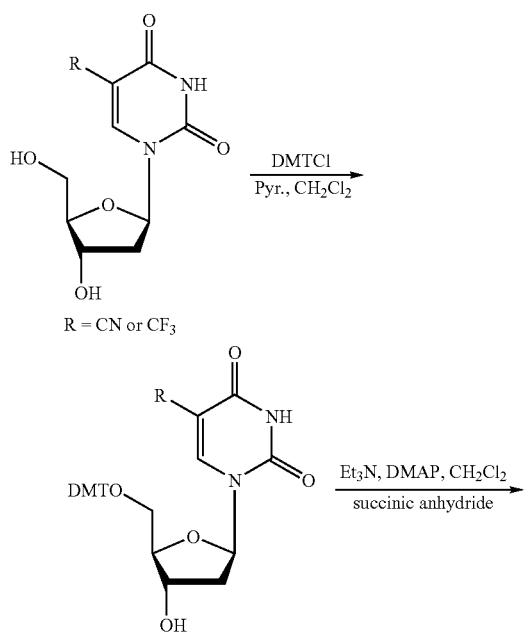

Scheme 1

-continued

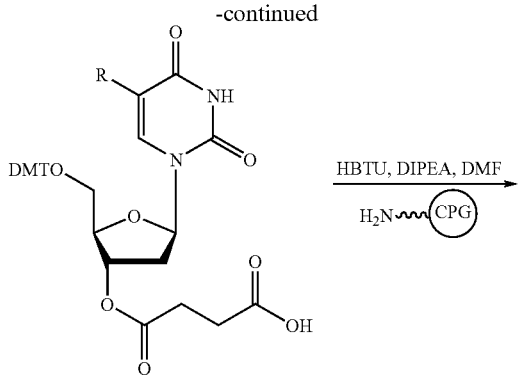

5-Trifluoromethyl-5'-dimethoxytrityl-2'-deoxyuridine

To a stirred solution of 250 mg of 5-trifluoromethyl-2'deoxyuridine (5-Tf-dU) in 20 mL of dry pyridine at 0° C. was added 227 mg of dimethoxytrityl chloride (DMT-Cl) and 10 mg of 4-dimethylaminopyridine (DMAP). The reaction was stirred for 5 hours at room temperature when a second portion of 144 mg of DMT-Cl was added. After stirring for 12 hours at room temperature, a third portion of 100 mg of DMT-Cl was added to the reaction. The reaction was stirred for an additional 4 hours at room temperature and then diluted with $CH_2Cl_2$, washed with water and dried over sodium sulfate ($Na_2SO_4$). The crude product was purified by silica gel column chromatography (0-10% methanol (MeOH) in $CH_2Cl_2$). 485 mg of the desired product (5'-DMT-5-Tf-dU) was obtained as a yellow foam (96% yield).

5-Trifluoromethyl-4'-(3-carboxypropionyl)-5'-dimethoxytrityl-2'-deoxy-uridine

To a stirred solution of 470 mg of DMT-5-Tfu, obtained above, in 20 mL of $CH_2Cl_2$ was added 133 mg of succinic anhydride, 48 mg of DMAP and 217 μL of triethylamine ($Et_3N$). After stirring for 12 hrs., the mixture was washed with 5% aqueous citric acid solution (1×30 mL) and saturated sodium chloride, NaCl, (1×30 mL). The organic layer was dried over $Na_2SO_4$ and evaporated to give 500 mg of 5-trifluoromethyl-4'-(3-carboxypropionyl)-5'-dimethoxytrityl-2'-deoxyuridine as a pale yellow foam.

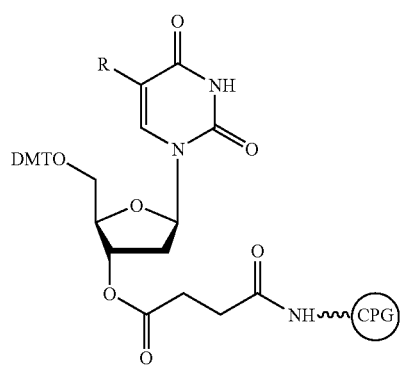

5-Trifluoromethyl-2'-deoxyuridine CPG

To a solution of 400 mg of 5-trifluoromethyl-4'-(3-carboxypropionyl)-5'-di-methoxytrityl-2'-deoxyuridine in 20 mL of dimethylformamide (DMF) was added 98 mg of 2-(1H-benzotriazole-1-yl)-1,1,3,3-tetramethyluronium hexafluorophosphate (HBTU), 135 μL of diisopropylethyl amine (DIPEA) and 7 g of CPG (37 μM/g). The mixture was shaken for 16 hours and then washed with DMF (3×50 mL), THF (3×30 mL) acetonitrile, $CH_3CN$, (2×30 mL) and $CH_2Cl_2$ (2×30 mL). The 5-trifluoromethyl-2'-deoxyuridine CPG product was dried under high vacuum for 4 hours.

5-Cyano-5'-dimethoxytrityl-2'-deoxyuridine

To a stirred solution of 506 mg of 5-cyano-2'deoxyuridine (5-CN-dU) in 124 mL of dry pyridine at 0° C. was added 813 mg of DMT-Cl and 49 mg of DMAP. The reaction was stirred for 12 hours at room temperature and then diluted with $CH_2Cl_2$, washed with water and dried over sodium sulfate ($Na_2SO_4$). The crude product was purified by silica gel column chromatography (10% MeOH in $CH_2Cl_2$). 710 mg of the desired product (5'-DMT-5-CN-dU) was obtained (64% yield).

5-Cyano-4'-(3-carboxypropionyl)-5'-dimethoxytrityl-2'-deoxyuridine

To a stirred solution of 310 mg of DMT-5-CN-dU, obtained above, in 7.5 mL of $CH_2Cl_2$ was added 100 mg of succinic anhydride, 34 mg of DMAP and 167 μL of $Et_3N$. After stirring for 12 hours at room temperature, the solvent was evaporated to give crude 5-Cyano-4'-(3-carboxypropionyl)-5'-dimethoxytrityl-2'-deoxyuridine which was used in the next step without further purification.

5-Cyano-2'-deoxyuridine CPG

To a solution of crude 5-trifluoromethyl-4'-(3-carboxypropionyl)-5'-dimethoxytrityl-2'-deoxyuridine in 15 mL of DMF was added 212 mg of HBTU, 145 μL of DIPEA and 7.5 g of CPG (37 μM/g). The mixture was stirred for 1 hour and then washed with DMF (3×50 mL), THF (3×30 mL) and $CH_2Cl_2$ (2×30 mL). The 5-trifluoromethyl-2'-deoxyuridine CPG product was dried under high vacuum.

3'-Terminal oligonucleotides of 5-cyano-2'-deoxyuridine, 5-trifluoromethyl-2'-deoxyuridine, and 5-fluoro-2'-deoxyuridine As mentioned above, automated DNA synthesis was carried out on an ABI 394 DNA synthesizer at a 0.2 μmol scale following the standard protocol. Oligonucleotides were purified by reversed phase HPLC on an Agilent 1100 HPLC system. To that end, the oligonucleotides shown in Tables 1-4 were synthesized. Forward primer AGTFcT and reverse primer AGTRcT amplify part of the human angiotesinogen gene (AGT, 125 bp). Forward primer LIGFcT and reverse primer LIGRcT amplify part of the human DNA ligase I gene (LIG, 82 bp). Forward primer D10SFcT and reverse primer D10SRcT amplify part of human chromosome 10 clone RP11-143D9 (D10S, 102 bp).

TABLE 1

| Primers | | | |
|---|---|---|---|
| X = T | X = 5-Cyano-2'-deoxyuridine | Primer Sequences | |
| AGTFcT | AGTFcT-CN | GGTCAGTTAATAACCACCTTTCACCCX | SEQ ID NO: 1 |
| AGTRcT | AGTRcT-CN | GCCAGGAGGCAGAGGATGGX | SEQ ID NO: 2 |
| LIGFcT | LIGFcT-CN | GGAGACCCCGAAAGAAAGCCX | SEQ ID NO: 3 |
| LIGRcT | LIGRcT-CN | AGGCGTGGTGGGCTGGX | SEQ ID NO: 4 |
| D10SFcT | D10SFcT-CN | CATATCTCACTCCTAAAACCCACAGGX | SEQ ID NO: 5 |
| D10SRcT | D10SRcT-CN | CAGACACCTACCACCTGCCCX | SEQ ID NO: 6 |

TABLE 2

| Primers | | | |
|---|---|---|---|
| X = T | X = 5-Trifluoromethyl-2'-deoxyuridine | Primer Sequences | |
| LIGFcT | LIGFcT-CF$_3$ | GGAGACCCCGAAAGAAAGCCX | SEQ ID NO: 7 |
| LIGRcT | LIGRcT-CF$_3$ | AGGCGTGGTGGGCTGGX | SEQ ID NO: 8 |

TABLE 3

| Primers | | | |
|---|---|---|---|
| X = T | X = 5-Fluoro-2'-deoxyuridine | Primer Sequences | |
| AGTFcT | AGTFcT-F | GGTCAGTTAATAACCACCTTTCACCCX | SEQ ID NO: 9 |
| AGTRcT | AGTRcT-F | GCCAGGAGGCAGAGGATGGX | SEQ ID NO: 10 |
| LIGFcT | LIGFcT-F | GGAGACCCCGAAAGAAAGCCX | SEQ ID NO: 11 |
| LIGRcT | LIGRcT-F | AGGCGTGGTGGGCTGGX | SEQ ID NO: 12 |

TABLE 4

| Primers | | | |
|---|---|---|---|
| X = T | X = 5-CN-2'-deoxyuridine | Primer Sequences | |
| Lamda-FcG | Lamda-FcG-5-CN | ATCAGAAACGAACGCATCATCAAGX | SEQ ID NO: 13 |
| Lamda-RcG | Lamda-RcG-5-CN | AAACAGCCACAAAGCCAGCCGGAAX | SEQ ID NO: 14 |

A second set of primers designed for amplification of AGT were prepared as described above. Each set having a 3' terminus of either 5-CN-dU, 5-CF$_3$-dU or 5-F-dU as shown below in Tables 4-6.

TABLE 5

| Primers | | | |
|---|---|---|---|
| X = T | X = 5-Cyano-2'-deoxyuridine | Primer Sequences | |
| AGTFcT | AGTFcT-CN | GCTCTCTGGACTTCACAGAACTGGAX | SEQ ID NO: 15 |
| AGTRcT | AGTRcT-CN | CCTTACCTTGGAAGTGGACGTAGGX | SEQ ID NO: 16 |

TABLE 6

| Primers | | | |
|---|---|---|---|
| X = T | X = 5-CF$_3$-2'-deoxyuridine | Primer Sequences | |
| AGTFcT | AGTFcT-CF$_3$ | GCTCTCTGGACTTCACAGAACTGGAX | SEQ ID NO: 17 |
| AGTRcT | AGTRcT-CF$_3$ | CCTTACCTTGGAAGTGGACGTAGGX | SEQ ID NO: 18 |

TABLE 7

| Primers | | | |
|---|---|---|---|
| X = T | X = 5-Fluoro-2'-deoxyuridine | Primer Sequences | |
| AGTFcT | AGTFcT-F | GCTCTCTGGACTTCACAGAACTGGAX | SEQ ID NO: 19 |
| AGTRcT | AGTRcT-F | CCTTACCTTGGAAGTGGACGTAGGX | SEQ ID NO: 20 |

5-Cyano-2'-deoxyuridine phosphoramidite

Scheme 2

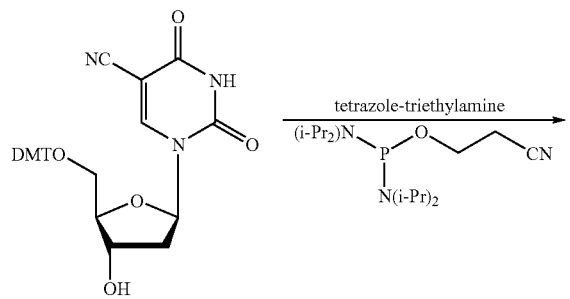

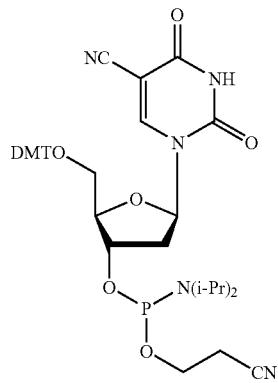

To a stirred solution of 250 mg of 5'-DMT-5-CN-dU in 20 mL $CH_2Cl_2$ was added 8 mg of tetrazole-triethylamine and 190 µL of 2-cyanoethyl-tetraisopropyl-phosphoramidite ($[(i-Pr)_2N]_2POCH_2CH_2CN$). The mixture was stirred at room temperature for 12 hours and the solvent removed under vacuum. The crude product was purified by silica gel chromatography (25/25/1 $CH_2Cl_2/CH_3CN/Et_3N$) to give 290 mg of 5-cyano-2'-deoxyuridine phosphoramidite (85% yield).

5-cyano-2'-deoxyuridine Containing Oligonucleotides

As mentioned above, automated DNA synthesis was carried out on an ABI 394 DNA synthesizer at a 0.2 µmol scale following the standard protocol. Oligonucleotides were purified by reversed phase HPLC on an Agilent 1100 HPLC system. To that end, the oligonucleotides shown in rows 2, 3 and 5 of Tables 7-8 were synthesized using 5-cyano-2'-deoxyuridine phosphoramidite to incorporate 5-cyano-2'-deoxyuridine at positions other than the 3' terminus, and the oligonucleotides having 5-cyano-2'-deoxyuridine at the 3' terminus were synthesized as described above.

TABLE 8

| Primers | | | |
|---|---|---|---|
| X = T | X = 5-Cyano-2'-deoxyuridine | Primer Sequences | |
| AGTFcT-short | AGTFcT-short-1-CN | GGTCAGTTAATAACCACCTTX | SEQ ID NO: 21 |
| | AGTFcT-short-2-CN | GGTCAGTTAATAACCACCTXT | SEQ ID NO: 22 |
| | AGTFcT-short-3-CN | GGTCAGTTAATAACCACCXTT | SEQ ID NO: 23 |
| AGTRcT | AGTRcT-CN | GCCAGGAGGCAGAGGATGGX | SEQ ID NO: 24 |
| | AGTRcT-4-CN | GCCAGGAGGCAGAGGAXGGT | SEQ ID NO: 25 |

TABLE 9

| Primers | | | |
|---|---|---|---|
| X = T | X = 5-Cyano-2'-deoxyuridine | Primer Sequences | |
| AGTFcT | AGTFcT-1-CN | CTCACCCTCATGGCCTCATTX | SEQ ID NO: 26 |
| | AGTFcT-2-CN | CTCACCCTCATGGCCTCATXT | SEQ ID NO: 27 |
| | AGTFcT-3-CN | CTCACCCTCATGGCCTCAXTT | SEQ ID NO: 28 |
| | AGTRcT-4-CN | ACCTCCCCAACGGCCAXAAT | SEQ ID NO: 29 |

Amplifications

All gDNA amplifications were carried out with 5000 copies of gDNA per 15 μL reaction and all λ-DNA amplifications were carried out with 1500 copies of gDNA per 15 μL reaction.

Amplification Reaction Condition #1:

Amplifications were carried out in 15 μL reactions using either unmodified and/or modified primers containing the following reagents:

SYBR® Green PCR Master Mix (Applied Biosystems, P/N 4309155)

900 nmoles of each forward and reverse primer water for no template control (NTC) experiments or 15 ng genomic DNA (Applied Biosystems, P/N 403062)

Amplification Reaction Condition #2:

Amplifications were carried out in 15 μL reactions using either unmodified and/or modified primers containing the following reagents:

10 mM Tris-HCl buffer, pH 8.3

50 mM KCl, 3 mM $MgCl_2$, 0.01% v/v gelatin 0.2 mM dATP, 0.2 mM dCTP, 0.2 mM dGTP, and 0.4 mM dUTP 0.025 unit/μL AmpliTaq Gold® DNA polymerase (Applied Biosystems, P/N N808-0107)

200 nM of each forward and reverse primer water for no template control (NTC) experiments or 15 ng genomic DNA (Applied Biosystems, P/N 403062)

Amplification Reaction Condition #3:

Amplifications were carried out in 15 μL reactions using either unmodified and/or modified primers containing the following reagents:

10 mM Tris-HCl buffer, pH 8.3

50 mM KCl, 3 mM $MgCl_2$, 0.01% v/v gelatin 0.2 mM dATP, 0.2 mM dCTP, 0.2 mM dGTP, and 0.4 mM dUTP 0.025 unit/μL AmpliTaq® DNA polymerase (Applied Biosystems, P/N N808-0158)

200 nM of each forward and reverse primer water for no template control (NTC) experiments or 15 ng genomic DNA (Applied Biosystems, P/N 403062)

The progress of all PCR reactions was monitored in real time by SYBR® Green assay on an ABI PRISM 7900HT Sequence Detection System (Applied Biosystems; Foster City, Calif.) as described in *SYBR® Green PCR Master Mix and RT-PCR: Protocol* (Applied Biosystems, 2002).

Amplification Reaction Analysis:

All amplification products were analyzed by gel electrophoresis as follows. PCR reaction mixture (15 μL) was diluted with 5 μL nuclease-free water. This solution was loaded along with 25 bp DNA ladder into wells of 4% agarose gel (Invitrogen, P/N G5018-04). Electrophoresis was carried out at 12 V DC at 880 mA for 30 minutes. Ethidium bromide stained bands of dsDNA were visualized using UV irradiation and quantified by AlphaDigDoc 1000 software (Alpha Innotech; San Leandro, Calif.) equipped with a Kodak digital camera.

Thermal Cycling:
Thermal Cycling Protocol #1:

Amplification temperature cycling was carried out using the following thermal cycling protocol.

TABLE 10

| | Pre-reaction incubation | AmpliTaq Gold® Activation | 50 Cycles | | |
|---|---|---|---|---|---|
| | | | Denature | Anneal/Extend | |
| Temperature (° C.) | 50 | 95 | 95 | 60 | 72 |
| Time | 2 min | 10 min | 15 sec | 30 sec | 30 sec |

Thermal Cycling Protocol #2:

Amplification temperature cycling was carried out using the following thermal cycling protocol.

TABLE 11

| | AmpliTaq Gold® | 50 Cycles | |
|---|---|---|---|
| | Activation | Denature | Anneal/Extend |
| Temperature (° C.) | 95 | 95 | 60 | 72 |
| Time | 10 min | 15 sec | 30 sec | 30 sec |

Thermal Cycling Protocol #3:

Amplification temperature cycling was carried out using the following thermal cycling protocol.

TABLE 12

| | AmpliTaq Gold® | 50 Cycles | |
|---|---|---|---|
| | Activation | Denature | Anneal/Extend |
| Temperature (° C.) | 95 | 95 | 60 | 72 |
| Time | 2 min | 15 sec | 30 sec | 30 sec |

Thermal Cycling Protocol #4:

Amplification temperature cycling was carried out using the following thermal cycling protocol.

TABLE 13

| | AmpliTaq Gold® | 50 Cycles | |
|---|---|---|---|
| | Activation | Denature | Anneal/Extend |
| Temperature (° C.) | 93 | 93 | 60 | 72 |
| Time | 2 min | 60 sec | 50 sec | 90 sec |

Amplifications Using 3'-Terminus Modified Primers:

5-Cyano-2'-deoxyuridine 3'-Terminal Primers/AmpliTaq Gold®

Amplification reactions using 3'-terminal 5-cyano-2'-deoxyuridine containing primers, shown in Table 1, were carried out under Amplification Reaction Condition #1 according to Thermal Cycling Protocol #1.

For each primer pair, amplification reactions using unmodified and 3'-modified primers were run with gDNA corresponding to the primer pair. Additionally, amplification reactions using unmodified and 3'-modified primers were run without any template as no template control (NTC) reactions.

Gel electrophoresis analysis was carried out as described above. Gel electrophoresis showed a significant amount of non-specific amplification product at about 40-50 bp, depending on the primer set used, in NTC amplifications with unmodified primers indicating the formation of primer-dimer amplicons. On the otherhand, significantly decreased primer-dimer amplicon formation was observed in gel electrophoresis images of NTC amplifications using 3'-modified primers. Gel electrophoresis of gDNA template amplification reactions using unmodified primers clearly showed a band corresponding to the desired template amplicon and also showed a band at corresponding to primer-dimer amplicon formation.

Amplification of AGT template using unmodified primers clearly showed a band at about 125 bp corresponding to the desired template amplicon and also showed a band at about 50 bp corresponding to primer-dimer amplicon formation. On the otherhand, amplification of AGT template using 3'-modified primers clearly showed a band at about 125 bp corresponding to the desired template amplicon but also showed significantly decreased primer-dimer amplicon formation.

Real time PCR monitoring showed that the AGT gDNA amplification efficiencies using unmodified- and 3'-modified- primers were similar. On the otherhand, while the NTC amplification using unmodified primers gave a $C_t$ value of about 37, NTC amplification using 5-cyano-2'-dU modified primers did not give a measurable signal until after the $44^{th}$ cycle.

Amplification of LIG template using unmodified primers clearly showed a band at about 80 bp corresponding to the desired template amplicon and also showed a band at about 40 bp corresponding to primer-dimer amplicon formation. On the otherhand, amplification of LIG template using 3'-modified primers clearly showed a band at about 80 bp corresponding to the desired template amplicon but also showed significantly decreased primer-dimer amplicon formation.

Amplification of D10S template using unmodified primers clearly showed a band at about 100 bp corresponding to the desired template amplicon and also showed a band at about 50 bp corresponding to primer-dimer amplicon formation. On the otherhand, amplification of D10S template using 3'-modified primers clearly showed a band at about 100 bp corresponding to the desired template amplicon but also showed significantly decreased primer-dimer amplicon formation.

Real time PCR monitoring showed similar results. In all cases, $C_t$ values for NTC amplifications with 3'-modified primers were significantly higher than $C_t$ values for NTC amplifications using unmodified primers indicating a suppression of primer-dimer amplification. In addition, $C_t$ values for each desired amplicon were similar between the unmodified and 3' modified primers indicating that amplification efficiency was not compromised by 3' modification.

5-Trifluoromethyl-2'-deoxyuridine 3'-Terminal Primers/AmpliTaq Gold®

Amplification reactions using 3'-terminal 5-trifluoromethyl-2'-deoxyuridine containing primers, shown in Table 2, were carried out under Amplification Reaction Condition #1 according to Thermal Cycling Protocol #1. Forward primer LIGFcT and reverse primer LIGRcT amplify part of the human DNA ligase I gene (LIG, 82 bp).

Amplification reactions using unmodified and 3'-modified primers were run with gDNA. Additionally, amplification reactions using unmodified and 3'-modified primers were run without any template as no template control (NTC) reactions.

Gel electrophoresis analysis was carried out as described above. Gel electrophoresis showed a significant amount of non-specific amplification product at about 40 bp in NTC amplifications with unmodified primers indicating the formation of primer-dimer amplicons. On the otherhand, significantly decreased primer-dimer amplicon formation was observed in gel electrophoresis images of NTC amplifications using 3'-modified primers. Gel electrophoresis of gDNA template amplification reactions using unmodified primers clearly showed a band corresponding to the desired template amplicon and also showed a band at corresponding to primer-dimer amplicon formation.

Amplification of LIG template using unmodified primers clearly showed a band at about 80 bp corresponding to the desired template amplicon and also showed a band at about 40 bp corresponding to primer-dimer amplicon formation. On the otherhand, amplification of LIG template using 3'-modified primers clearly showed a band at about 80 bp corresponding to the desired template amplicon but also showed significantly decreased primer-dimer amplicon formation.

Real time PCR monitoring showed that the LIG gDNA amplification efficiencies using unmodified- and 3'-modified- primers were similar. On the otherhand, while the NTC amplification using unmodified primers gave a $C_t$ value of about 40, NTC amplification using 5-trifluoromethyl-2'-dU modified primers provided no measurable signal through the 50-cycle amplification.

5-Fluoro-2'-deoxyuridine 3'-Terminal Primers/AmpliTaq Gold®

Amplification reactions using 3'-terminal 5-fluoro-2'-deoxyuridine containing primers, shown in Table 3, were carried out under Amplification Reaction Condition #1 according to Thermal Cycling Protocol #2. Forward primer AGTFcT and reverse primer AGTRcT amplify part of the human angiotesinogen gene (AGT, 125 bp). Forward primer LIGFcT and reverse primer LIGRcT amplify part of the human DNA ligase I gene (LIG, 82 bp).

For each primer pair, amplification reactions using unmodified and 3'-modified primers were run with gDNA corresponding to the primer pair. Additionally, amplification reactions using unmodified and 3'-modified primers were run without any template as no template control (NTC) reactions.

Gel electrophoresis analysis was carried out as described above. Gel electrophoresis showed a significant amount of non-specific amplification product at about 40-50 bp, depending on the primer set used, in NTC amplifications with unmodified primers indicating the formation of primer-dimer amplicons. On the otherhand, significantly decreased primer-dimer amplicon formation was observed in gel electrophoresis images of NTC amplifications using 3'-modified primers. Gel electrophoresis of gDNA template amplification reactions using unmodified primers clearly showed a band corresponding to the desired template amplicon and also showed a band at corresponding to primer-dimer amplicon formation.

Amplification of AGT template using unmodified primers clearly showed a band at about 125 bp corresponding to the desired template amplicon and also showed a band at about 50 bp corresponding to primer-dimer amplicon formation. On the otherhand, amplification of AGT template using 3'-modified primers clearly showed a band at about 125 bp corresponding to the desired template amplicon but also showed significantly decreased primer-dimer amplicon formation.

Real time PCR monitoring showed that the AGT gDNA amplification efficiencies using unmodified- and 3'-modified- primers were very similar. On the otherhand, while the NTC amplification using unmodified primers gave a $C_t$ value of about 36, NTC amplification using 5-fluoro-2'-dU modified primers did not give a measurable signal until almost the $40^{th}$ cycle.

Amplification of LIG template using unmodified primers clearly showed a band at about 80 bp corresponding to the desired template amplicon and also showed a band at about 40 bp corresponding to primer-dimer amplicon formation. On the otherhand, amplification of LIG template using 3'-modified primers clearly showed a band at about 80 bp corresponding to the desired template amplicon but also showed significantly decreased primer-dimer amplicon formation.

Real time PCR monitoring showed that the LIG gDNA amplification efficiencies using unmodified- and 3'-modified-primers were similar. On the otherhand, while the NTC amplification using unmodified primers gave a $C_t$ value of about 40, NTC amplification using 5-fluoro-2'-dU modified primers did not give a measurable signal until after the $49^{th}$ cycle.

5-Cyano-2'-deoxyuridine Containing Primers/AmpliTaq Gold®

Amplification reactions using 5-cyano-2'-deoxyuridine containing primers, shown in Table 8, were carried out under Amplification Reaction Condition #1 according to Thermal Cycling Protocol #2.

For each primer pair, amplification reactions using unmodified and modified primers were run with gDNA corresponding to the primer pair. Additionally, amplification reactions using unmodified and 3'-modified primers were run without any template as no template control (NTC) reactions.

Gel electrophoresis analysis was carried out as described above. Gel electrophoresis of amplification using unmodified AGTFcT-short primer showed a significant amount of non-specific amplification product at about 50 bp in NTC amplifications indicating the formation of primer-dimer amplicons. On the otherhand, no primer-dimer amplicon formation was observed in gel electrophoresis images of NTC amplifications using AGTFcT-short-1-CN, AGTFcT-short-2-CN, AGTFcT-short-3-CN modified primers.

Real time PCR monitoring of NTC amplification using unmodified primers gave a $C_t$ value of about 34. On the other hand, NTC amplification using 5-cyano-2'-dU modified primers AGTFcT-short-1-CN, AGTFcT-short-2-CN, and AGTFcT-short-3-CN gave no measurable signal through the 50-cycle amplification.

Amplification of AGT template using AGTFcT-short-1-CN, AGTFcT-short-2-CN, AGTFcT-short-3-CN modified primers clearly showed a band at about 125 bp corresponding to the desired template amplicon but also showed no primer-dimer amplicon formation.

Real time PCR monitoring showed that the AGT gDNA amplification efficiencies using unmodified- and 5-CN-dU containing primers AGTFcT-short-1-CN, AGTFcT-short-2-CN and AGTFcT-short-3-CN were similar, with all $C_t$ values falling between 26 and 29 cycles.

Gel electrophoresis of amplification using unmodified AGT primer showed a significant amount of non-specific amplification products between about 40 bp and 80 bp in NTC amplifications indicating the formation of primer-dimer amplicons. On the otherhand, primer-dimer amplicon formation was significantly decreased in gel electrophoresis images of NTC amplifications using AGTFcT-4-CN modified primer.

Likewise in the AGT gDNA template amplification, gel electrophoresis of amplification using unmodified AGTFcT primer showed a band at about 125 bp attributed to the desired amplicon as well as a significant amount of non-specific amplification products between about 50 bp and 80 bp in gDNA amplifications indicating the formation of primer-dimer amplicons. On the otherhand, primer-dimer amplicon formation was not seen in gel electrophoresis images of NTC amplifications using AGTFcT-4-CN modified primers.

Real time PCR monitoring showed that the AGT gDNA amplification efficiencies using unmodified- and 5-CN-dU containing primer AGTFcT-4-CN were very similar, with $C_t$ values 28 and 29 cycles respectively. Real time monitoring of the NTC amplifications of unmodified-AGT and AGTFcT-4-CN primers gave $C_t$ values of 38 and 43 cycles respectively.

5-Cyano-2'-deoxyuridine, 5-CF$_3$-2-deoxyuridine and 5-Fluoro-2'deoxyuridine 3'-Terminal Modified Primers/AmpliTaq®

Amplification reactions using 3'-terminal modified primers, shown in Table 5-7, were carried out under Amplification Reaction Condition #3 according to Thermal Cycling Protocol #3.

For each primer pair, amplification reactions using unmodified and 3'-modified primers were run with gDNA corresponding to the primer pair. Additionally, amplification reactions using unmodified and 3'-modified primers were run without any template as no template control (NTC) reactions.

Gel electrophoresis analysis was carried out as described above. Gel electrophoresis of amplification using unmodified primer showed a significant amount of non-specific amplification product at about 60 bp in NTC amplifications with unmodified primers indicating the formation of primer-dimer amplicons. On the otherhand, no primer-dimer amplicon formation was observed in gel electrophoresis images of NTC amplifications using 3'-terminal modified primers.

Amplification of AGT template using 5-CN-dU, 5-CF$_3$-dU and 5-F-dU 3'-terminal modified primers clearly showed a band at about 125 bp corresponding to the desired template amplicon but also showed no primer-dimer amplicon formation.

5-Cyano-2'-deoxyuridine Containing Primers/AmpliTaq®

Amplification reactions using 5-cyano-2'-deoxyuridine containing primers, shown in Table 9, were carried out under Amplification Reaction Condition #3 according to Thermal Cycling Protocol #3.

For each primer pair, amplification reactions using unmodified and 3'-modified primers were run with gDNA corresponding to the primer pair. Additionally, amplification reactions using unmodified and 3'-modified primers were run without any template as no template control (NTC) reactions.

Gel electrophoresis analysis was carried out as described above. Gel electrophoresis of amplification using unmodified AGTFcT primer showed a significant amount of non-specific amplification product at about 50 bp in NTC amplifications with unmodified primers indicating the formation of primer-dimer amplicons. On the otherhand, no primer-dimer amplicon formation was observed in gel electrophoresis images of NTC amplifications using AGTFcT-1-CN, AGTFcT-2-CN, AGTFcT-3-CN or AGTRcT-4-CN modified primers.

Amplification of AGT template using AGTFcT-1-CN, AGTFcT-2-CN, AGTFcT-3-CN or AGTRcT-4-CN modified primers clearly showed a band at about 125 bp corresponding to the desired template amplicon but also showed no primer-dimer amplicon formation.

λ-DNA Amplifications:

To test whether 3'-modified primers of the present teachings could reduce non-specific amplification without effecting amplification efficiency of longer amplicons, λ-DNA was used as a template with primers designed to make a 1700 bp target amplicon.

5-Cyano-2'-deoxyuridine λ-DNA Amplification

Amplification reactions using 3'-terminal 5-cyano-2'-deoxyuridine containing primers, shown in Table 4, were carried out under Amplification Reaction Condition #2 according to Thermal Cycling Protocol #4. Both real time analysis and gel electrophoresis showed that even with longer amplicons, 3'-modification with 5-CN-2'-deoxyuridine resulted in significant reduction in primer-dimer amplification without adversely effecting target amplification efficiency.

We claim:

1. A purified single-stranded polynucleotide primer comprising at least one modified pyrimidine nucleobase of the structure

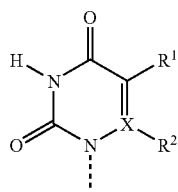

wherein

X is N or C, $R^1$ is selected from —H, —F, —Cl, —Br, $C_1$-$C_6$ alkyl, $C_1$-$C_6$ substituted alkyl, $C_3$-$C_{10}$ aryl, $C_3$-$C_{10}$ substituted aryl, —CF$_3$, —CF$_2$H, —CF$_2$CH$_3$, —CF$_2$CF$_3$, —CCl$_3$, —CN, —CHO, —CO$_2$R, —SO$_3$R, —PO$_3$RR, —C(O)NRR, azido, and —NO$_2$ where each R is independently —H, $C_1$-$C_6$ alkyl or $C_3$-$C_{10}$ aryl or alkylaryl, and $R^2$ is selected from —H, —F, —Cl, —Br, $C_1$-$C_6$ alkyl, $C_1$-$C_6$ substituted alkyl, $C_3$-$C_{10}$ aryl, $C_3$-$C_{10}$ substituted aryl, —CF$_3$, —CF$_2$H, —CF$_2$CH$_3$, —CF$_2$CF$_3$, —CCl$_3$, —CN, —CHO, —CO$_2$R, —SO$_3$R, —PO$_3$RR, —C(O)NRR, azido, and —NO$_2$ where each R is independently H, $C_1$-$C_6$ alkyl or $C_3$-$C_{10}$ aryl or alkylaryl, wherein at least one of $R^1$ or $R^2$ is an electron withdrawing substituent or X is N, such that when X is N, $R^2$ is absent, at least one said modified pyrimidine nucleobase is no more than 4 nucleotides from the 3' terminus of the primer, and said purified single-stranded polynucleotide primer comprising said modified pyrimidine nucleobase now complementary to a target sequence.

2. The polynucleotide primer according to claim 1, wherein X is C.

3. The polynucleotide primer according to claim 2, wherein $R^2$ is —H.

4. The polynucleotide primer according to claim 3, wherein $R^1$ is selected from —F, —Cl, —Br, —CO$_2$R, —NO$_2$, —CHO, —COCH$_3$, —CF$_3$, —CF$_2$H, azido, and —CN.

5. The polynucleotide primer according to claim 4, wherein $R^1$ is —F.

6. The polynucleotide primer according to claim 4, wherein $R^1$ is —CF$_3$.

7. The polynucleotide primer according to claim 4, wherein $R^1$ is —CN.

8. The polynucleotide primer according to claim 4, wherein $R^1$ is —Cl.

9. The polynucleotide primer according to claim 4, wherein $R^1$ is —$CO_2R$.

10. The polynucleotide primer according to claim 4, wherein $R^1$ is —$NO_2$.

11. The polynucleotide primer according to claim 4, wherein $R^1$ is —CHO.

12. The polynucleotide primer according to claim 4, wherein $R^1$ is —$COCH_3$.

13. The polynucleotide primer according to claim 4, wherein $R^1$ is —$CF_2H$.

14. The polynucleotide primer according to claim 4, wherein $R^1$ is —Br.

15. The polynucleotide primer according to claim 1, wherein $R^2$ is selected from —F, —Cl, —Br, —$CO_2R$, —$NO_2$, —CHO, —$SO_3R$, —$PO_3RR$—$C(O)CH_3$, —$CF_3$, —$CF_2H$, azido, and —CN.

16. The polynucleotide primer of claim 1, wherein at least one modified nucleotide is the 3' terminal nucleotide of the polynucleotide.

17. The polynucleotide primer of claim 1, wherein at least one modified pyrimidine nucleobase is no more than 3 nucleotides from the 3' terminus of the polynucleotide.

18. The polynucleotide primer of claim 1, wherein at least one modified pyrimidine nucleobase is no more than 2 nucleotides from the 3' terminus of the polynucleotide.

19. The polynucleotide primer of claim 1, wherein the polynucleotide is extendable at the 3'-terminus.

* * * * *